(12) United States Patent
Zhang et al.

(10) Patent No.: US 11,530,245 B2
(45) Date of Patent: Dec. 20, 2022

(54) SPLIT INTEIN MEDIATED POLYMERIZATION AND PRODUCTION OF MUSSEL FOOT ADHESIVE PROTEIN MATERIALS

(71) Applicants: Fuzhong Zhang, St. Louis, MO (US); Eugene Kim, St. Louis, MO (US)

(72) Inventors: Fuzhong Zhang, St. Louis, MO (US); Eugene Kim, St. Louis, MO (US)

(73) Assignee: Washington University, St. Louis, MO (US)

( * ) Notice: Subject to any disclaimer, the term of this patent is extended or adjusted under 35 U.S.C. 154(b) by 149 days.

(21) Appl. No.: 16/554,171

(22) Filed: Aug. 28, 2019

(65) Prior Publication Data

US 2020/0071368 A1     Mar. 5, 2020

Related U.S. Application Data

(60) Provisional application No. 62/725,636, filed on Aug. 31, 2018.

(51) Int. Cl.
    *C07K 14/435*      (2006.01)
    *C12N 15/62*      (2006.01)

(52) U.S. Cl.
    CPC ........ *C07K 14/43504* (2013.01); *C12N 15/62* (2013.01); *C07K 2319/20* (2013.01); *C07K 2319/92* (2013.01)

(58) Field of Classification Search
None
See application file for complete search history.

(56) References Cited

U.S. PATENT DOCUMENTS

| | | | |
|---|---|---|---|
| 10,870,783 B2 * | 12/2020 | Lee | ............... C09J 189/00 |
| 2003/0013148 A1 | 1/2003 | Evans et al. | |
| 2011/0033891 A1 | 2/2011 | Cha et al. | |
| 2012/0202748 A1 | 8/2012 | Cha et al. | |
| 2014/0315276 A1 | 10/2014 | Albayrak et al. | |
| 2016/0220727 A1 * | 8/2016 | Lu | ............... C07K 14/43504 |

FOREIGN PATENT DOCUMENTS

| | | |
|---|---|---|
| EP | 2518081 A1 | 10/2012 |
| WO | 2013045632 A1 | 4/2013 |
| WO | WO-2017132580 A2 * | 8/2017 ......... A61K 47/6803 |

OTHER PUBLICATIONS

Cha, H.J., et al. 2008 Biotechnol J 3: 631-638. (Year: 2008).*
Wang, J., et al. 2018 Biotechnol J 13:1800146 (12 pages). (Year: 2018).*
Collier, J.H., et al. 2011 Biomaterials 32: 4198-4204. (Year: 2011).*
Bowen, C.H., et al. 2018 Biomacromolecules 19: 3853-3860. (Year: 2018).*
Stevens, A.J., et al. 2016 J Am Chem Soc 138: 2162-2165. (Year: 2016).*
Albayrak et al., "Direct polymerization of proteins", ACS Synth. Biol., 2014, vol. 3, pp. 353-362.
Evans et al., "The cyclization and polymerization of bacterially expressed proteins using modified self-splicing inteins", J. Biol. Chem. 1999, vol. 274, pp. 18359-18363.
Hwang et al., "Practical recombinant hybrid mussel bioadhesive fp-151", Biomaterials., 2007, vol. 28, pp. 3560-3568.
Choi et al., "Recombinant mussel adhesive protein fp-5 (MAP fp-5) as a bulk bioadhesive and surface coating material", Biofouling., 2011, vol. 27, No. 7, pp. 729-737.

* cited by examiner

*Primary Examiner* — Marsha Tsay
(74) *Attorney, Agent, or Firm* — Armstrong Teasdale LLP

(57) ABSTRACT

Mussels strongly adhere to a variety of surfaces by secreting byssal threads that contain mussel foot proteins (Mfps). Recombinant production of Mfps presents an attractive route for preparing advanced adhesive materials. Using synthetic biology strategies, Mfp5 together with Mfp5 oligomers containing two or three consecutive, covalently-linked Mfp5 sequences (named $Mfp5^2$ and $Mfp5^3$) were synthesized. Positive correlations were found between Mfp5 molecular weight and underwater adhesive properties, including adhesion force, adhesion work, protein layer thickness, and recovery distance. Dopa-modified $Mfp5^3$ displayed a high adhesion force ($201 \pm 36$ nN $\mu m^{-1}$) and a high adhesion work ($68 \pm 21$ fJ $\mu m^{-1}$) for 200 s cure times, higher than previously reported Mfp-mimetic adhesives. Results disclosed herein highlight the power of synthetic biology in producing biocompatible and highly adhesive Mfp-based materials.

11 Claims, 33 Drawing Sheets

Specification includes a Sequence Listing.

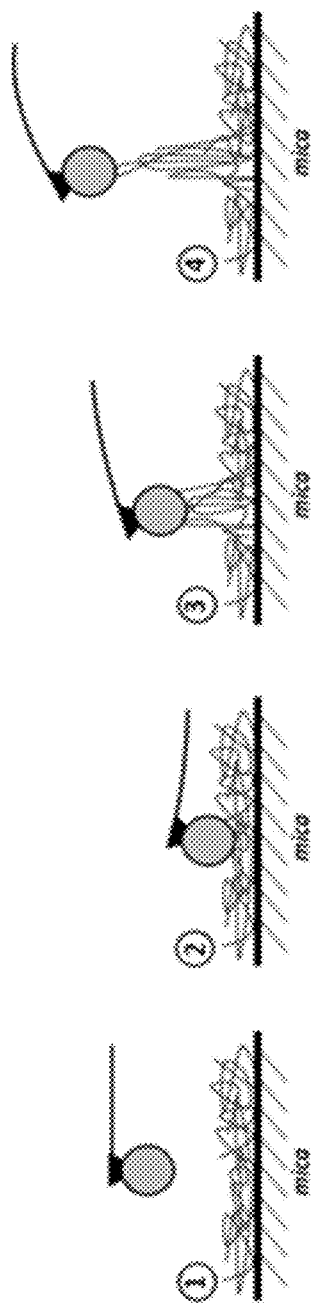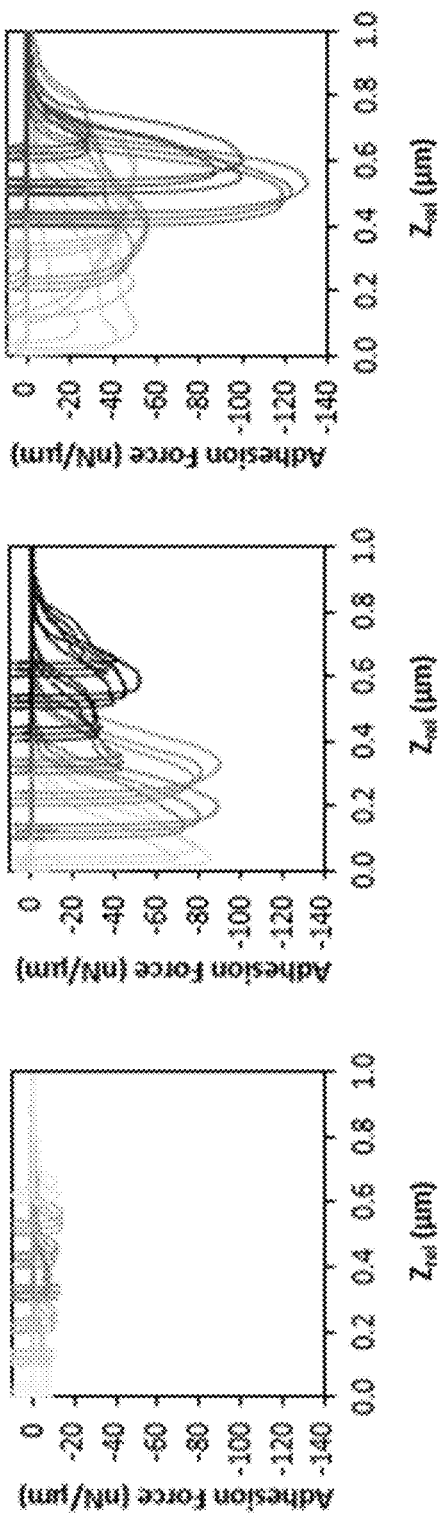
FIG. 8A  FIG. 8B  FIG. 8C  FIG. 8D

SEQUENCE LISTING

<160> NUMBER OF SEQ ID NOS: 19

<210> SEQ ID NO 1
<211> LENGTH: 33
<212> TYPE: DNA
<213> ORGANISM: Artificial Sequence
<220> FEATURE:
<223> OTHER INFORMATION: Synthesized plasmid

<400> SEQUENCE: 1
atggctaaga ctaaacatca tcaccatcat cac                                33

<210> SEQ ID NO 2
<211> LENGTH: 11
<212> TYPE: PRT
<213> ORGANISM: Artificial Sequence
<220> FEATURE:
<223> OTHER INFORMATION: Synthesized plasmid

<400> SEQUENCE: 2

Met Ala Lys Thr Lys His His His His His
1               5                   10

<210> SEQ ID NO 3
<211> LENGTH: 291
<212> TYPE: DNA
<213> ORGANISM: Escherichia coli

<400> SEQUENCE: 3
gctaagacta acatcatca ccatcaccac ggtggcggtg gcagcagatc tggatctagc      60
agcgaagagt ataaaggtgg ttactacccg ggcaacactt accactacca tagcggcggc    120
tcctaccacg gttccggcta tcacggtggc tacaaaggta atactacgg caaagcgaaa     180 aagtactact acaaatataa aaactccggc aaatacaagt atctgaagaa ggctcgtaaa    240
tatcaccgta aggttacaa aaagtattac ggcggtggtt cttctggatc c              291

<210> SEQ ID NO 4
<211> LENGTH: 513
<212> TYPE: DNA
<213> ORGANISM: Escherichia coli

<400> SEQUENCE: 4
gctaagacta acatcatca ccatcaccac ggtggcggtg gcagcagatc ttcaagtgaa      60
gaatataagg gcggctatta ccctgggaac acctaccatt accactcggg tggttcgtat    120
catggttccg gctaccatgg tggttacaag gggaagtatt atggtaaagc gaagaaatac    180
tattacaaat acaagaattc tggaaagtat aaatatctga aaaaagctcg caaatatcat    240

```
cgtaaaggat ataaaaaata ctatggaggt ggcagtagca gttccgaaga atataaaggg    300
ggttactacc ctggaaacac ttatcattat catagtggag gttcttacca tggcagtgga    360
tatcacggcg gttataaggg taagtattat gggaaagcca aaagtatta ctataagtac    420 aagaattctg gcaaatacaa gtacttgaag aaggctcgta agtaccaccg caaaggttac    480
aagaaatact atggaggcgg ttcaagtctc gag                                 513
```

<210> SEQ ID NO 5
<211> LENGTH: 132
<212> TYPE: DNA
<213> ORGANISM: Escherichia coli

<400> SEQUENCE: 5

```
aaaaaacata tggtcaagat cattagtcgt aagagtctgg gcactcaaaa cgtctacgat     60
attggagtag aaaaagatca taattttttg ctgaagaatg ggctggtggc ctctaactgc    120
ttcaacggta cc                                                        132
```

<210> SEQ ID NO 6
<211> LENGTH: 333
<212> TYPE: DNA
<213> ORGANISM: Escherichia coli

<400> SEQUENCE: 6

```
tccggagcag aatattgcct gtcttacgac acagagattc tgaccgttga atatggattc     60
cttcctatcg gtaagatcgt ggaggaacgg attgaatgca cagtctatac ggtagataaa    120
aatggctttg tgtatacaca acctattgct cagtggcata accggggaga acaggaagtt    180
ttcgaatact gcttagaaga cggttcgatt atccgtgcaa cgaaagatca caaatttatg    240
acgaccgacg gtcagatgtt accgattgat gagattttcg aacggggtt agacctgaaa    300 caagttgatg gtttgccgta aggatccaaa aaa                                 333
```

<210> SEQ ID NO 7
<211> LENGTH: 34
<212> TYPE: DNA
<213> ORGANISM: Artificial Sequence
<220> FEATURE:
<223> OTHER INFORMATION: Synthesized forward primer BglII-Mfp51-F

<400> SEQUENCE: 7

```
aaaaaaagat ctagcagcga agagtataaa ggtg                                 34
```

<210> SEQ ID NO 8
<211> LENGTH: 28
<212> TYPE: DNA
<213> ORGANISM: Artificial Sequence
<220> FEATURE:
<223> OTHER INFORMATION: Synthesized reverse primer BamHI-Mfp51-R

<400> SEQUENCE: 8

```
aaaaaaggat ccagaagaac caccgccg                                        28
```

<210> SEQ ID NO 9
<211> LENGTH: 39
<212> TYPE: DNA
<213> ORGANISM: Artificial Sequence
<220> FEATURE:
<223> OTHER INFORMATION: Synthesized forward primer BglII-Mfp52-F

<400> SEQUENCE: 9

```
aaaaaaagat cttcaagtga agaatataag ggcggctat                    39
```

<210> SEQ ID NO 10
<211> LENGTH: 40
<212> TYPE: DNA
<213> ORGANISM: Artificial Sequence
<220> FEATURE:
<223> OTHER INFORMATION: Synthesized reverse primer XhoI-Mfp52-R

<400> SEQUENCE: 10

```
aaaaaactcg agacttgaac cgcctccata gtatttcttg                   40
```

<210> SEQ ID NO 11
<211> LENGTH: 43
<212> TYPE: DNA
<213> ORGANISM: Artificial Sequence
<220> FEATURE:
<223> OTHER INFORMATION: Synthesized forward primer KpnI-Mfp51-F

<400> SEQUENCE: 11

```
aaaaaaggta ccagcagcga agagtataaa ggtggttact acc               43
```

<210> SEQ ID NO 12
<211> LENGTH: 34
<212> TYPE: DNA
<213> ORGANISM: Artificial Sequence
<220> FEATURE:
<223> OTHER INFORMATION: Synthesized reverse primer Kpn2I-Mfp51-R

<400> SEQUENCE: 12

```
aaaaaatccg gaagaagaac caccgccgta atac                         34
```

<210> SEQ ID NO 13
<211> LENGTH: 44
<212> TYPE: DNA
<213> ORGANISM: Artificial Sequence
<220> FEATURE:
<223> OTHER INFORMATION: Synthesized forward primer KpnI-Mfp52-F

<400> SEQUENCE: 13

```
aaaaaaggta cctcaagtga agaatataag ggcggctatt accc              44
```

<210> SEQ ID NO 14
<211> LENGTH: 44
<212> TYPE: DNA
<213> ORGANISM: Artificial Sequence
<220> FEATURE:
<223> OTHER INFORMATION: Synthesized reverse primer Kpn2I-Mfp52-R

<400> SEQUENCE: 14

```
aaaaaatccg gaacttgaac cgcctccata gtatttcttg taac              44
```

<210> SEQ ID NO 15
<211> LENGTH: 97
<212> TYPE: PRT
<213> ORGANISM: Escherichia coli

<400> SEQUENCE: 15

```
Ala Lys Thr Lys His His His His His His Gly Gly Gly Gly Ser Arg
 1               5                  10                  15

Ser Gly Ser Ser Ser Glu Glu Tyr Lys Gly Gly Tyr Tyr Pro Gly Asn
                20                  25                  30

Thr Tyr His Tyr His Ser Gly Gly Ser Tyr His Gly Ser Gly Tyr His
            35                  40                  45
```

```
Gly Gly Tyr Lys Gly Lys Tyr Tyr Gly Lys Ala Lys Lys Tyr Tyr
            50                  55                  60
Lys Tyr Lys Asn Ser Gly Lys Tyr Lys Tyr Leu Lys Lys Ala Arg Lys
 65                  70                  75                  80
Tyr His Arg Lys Gly Tyr Lys Lys Tyr Tyr Gly Gly Ser Ser Gly
                 85                  90                  95
Ser

<210> SEQ ID NO 16
<211> LENGTH: 171
<212> TYPE: PRT
<213> ORGANISM: Escherichia coli

<400> SEQUENCE: 16

Ala Lys Thr Lys His His His His His His Gly Gly Gly Ser Arg
 1               5                  10                  15
Ser Ser Ser Glu Glu Tyr Lys Gly Gly Tyr Tyr Pro Gly Asn Thr Tyr
                 20                  25                  30
His Tyr His Ser Gly Gly Ser Tyr His Gly Ser Gly Tyr His Gly Gly
                 35                  40                  45
Tyr Lys Gly Lys Tyr Tyr Gly Lys Ala Lys Lys Tyr Tyr Lys Tyr
            50                  55                  60
Lys Asn Ser Gly Lys Tyr Lys Tyr Leu Lys Lys Ala Arg Lys Tyr His
 65                  70                  75                  80
Arg Lys Gly Tyr Lys Lys Tyr Tyr Gly Gly Ser Ser Ser Glu
                 85                  90                  95
Glu Tyr Lys Gly Gly Tyr Tyr Pro Gly Asn Thr Tyr His Tyr His Ser
                100                 105                 110
Gly Gly Ser Tyr His Gly Ser Gly Tyr His Gly Gly Tyr Lys Gly Lys
                115                 120                 125
Tyr Tyr Gly Lys Ala Lys Lys Tyr Tyr Lys Tyr Lys Asn Ser Gly
                130                 135                 140
Lys Tyr Lys Tyr Leu Lys Lys Ala Arg Lys Tyr His Arg Lys Gly Tyr
145                 150                 155                 160
Lys Lys Tyr Tyr Gly Gly Ser Ser Leu Glu
                165                 170

<210> SEQ ID NO 17
<211> LENGTH: 104
<212> TYPE: PRT
<213> ORGANISM: Escherichia coli

<400> SEQUENCE: 17

Ala Glu Tyr Cys Leu Ser Tyr Asp Thr Glu Ile Leu Thr Val Glu Tyr
 1               5                  10                  15
Gly Phe Leu Pro Ile Gly Lys Ile Val Glu Glu Arg Ile Glu Cys Thr
                 20                  25                  30
Val Tyr Thr Val Asp Lys Asn Gly Phe Val Tyr Thr Gln Pro Ile Ala
                 35                  40                  45
Gln Trp His Asn Arg Gly Glu Gln Glu Val Phe Glu Tyr Cys Leu Glu
 50                  55                  60
Asp Gly Ser Ile Ile Arg Ala Thr Lys Asp His Lys Phe Met Thr Thr
 65                  70                  75                  80
Asp Gly Gln Met Leu Pro Ile Asp Glu Ile Phe Glu Arg Gly Leu Asp
                 85                  90                  95
Leu Lys Gln Val Asp Gly Leu Pro
```

```
                                  100

<210> SEQ ID NO 18
<211> LENGTH: 38
<212> TYPE: PRT
<213> ORGANISM: Escherichia coli

<400> SEQUENCE: 18

Val Lys Ile Ile Ser Arg Lys Ser Leu Gly Thr Gln Asn Val Tyr Asp
1               5                   10                  15

Ile Gly Val Glu Lys Asp His Asn Phe Leu Leu Lys Asn Gly Leu Val
                20                  25                  30

Ala Ser Asn Cys Phe Asn
        35

<210> SEQ ID NO 19
<211> LENGTH: 4
<212> TYPE: PRT
<213> ORGANISM: Artificial Sequence
<220> FEATURE:
<223> OTHER INFORMATION: Synthesized expression tag

<400> SEQUENCE: 19

Ala Lys Thr Lys
1
```

SPLIT INTEIN MEDIATED POLYMERIZATION AND PRODUCTION OF MUSSEL FOOT ADHESIVE PROTEIN MATERIALS

CROSS-REFERENCE TO RELATED APPLICATIONS

This application claims priority to U.S. Provisional Patent Application No. 62/725,636, filed on Aug. 31, 2018, which is hereby incorporated by reference in its entirety.

STATEMENT REGARDING FEDERALLY SPONSORED RESEARCH & DEVELOPMENT

This invention was made with government support under N00014-15-1-2515 awarded by the US Navy, Office of Naval Research. The government has certain rights in the invention.

SEQUENCE LISTING

The instant application contains a Sequence Listing which has been submitted electronically in ASCII form and is hereby incorporated by reference in its entirety. Said ASCII copy, created on Feb. 11, 2022, is named Sequence-Listing-V2_15060-1130_018745USNP.TXT and is 8,448 bytes in size.

BACKGROUND OF THE DISCLOSURE

Nature has evolved a wide array of protein-based materials and composites (e.g., silk, elastin, collagen) with mechanical properties and functions exceeding the performance of many synthetic polymers and even metal alloys. These remarkable properties arise from the multi-scale assembly of a narrow set of basic, repetitive peptide sequences. Engineering microbial cell factories for heterologous production of such proteins offers the opportunity to provide unlimited supplies of natural materials from cheap and renewable feedstocks (e.g., cellulosic biomass and simple sugars), presenting a sustainable and cost-effective approach to advanced material manufacturing. Further, editing protein sequences and engineering material assembly processes allow for tunable material properties and enable novel applications. Disclosed herein is a microbially-engineered process to produce strong adhesive mussel foot proteins (Mfps), and characterization properties of the synthesized Mfps.

Mfps secreted in the byssal threads of mussels have an extraordinary ability to adhere to various surfaces underwater, a feat which is unachievable by most chemical or synthetic adhesives. To date, seven main types of Mfps have been identified, and different Mfp types spatially organized at specific locations of the mussel byssal plaque have been found to serve different functions. While Mfp2 and Mfp4, which are localized at the core of the mussel byssal thread plaque, are mostly responsible for cohesive protein-protein interactions, the intrinsically disordered Mfp3 and Mfp5 are localized at the distal end of the plaque and play major roles in surface adhesion. FIGS. 1A-C are schematic representations of the design and production of strong underwater adhesives using engineered microbes. The distal end of the mussel plaque is abundant in Mfp5, whose DNA sequence is recoded for E. coli production using standard genetic parts. Mfp5 chains can adhere to various surfaces via multiple types of interactions, e.g., bidentate hydrogen bonding and metal complexation (FIG. 1B). Mfp5 can also cohesively interact with neighboring chains via bi-DOPA hydrogen bonding, aryloxyl radicalization crosslinking, and physical chain entanglements. Compared to low molecular weight (MW) proteins, high MW proteins are expected to chemically interact and entangle into a more robust network of interactions. Mfps have varying levels of 3,4-dihydroxyphenylalanine (DOPA), which arise from post-translational modification of tyrosine residues by tyrosinases, a group of natively-expressed hydroxylating enzymes. Extensive studies have illustrated the essential roles of DOPA in forming both adhesive protein-surface interactions via bidentate hydrogen bonding, metal complexation, and hydrophobic interactions, and in cohesive protein-protein interactions via bis- or tris-DOPA-$Fe^{3+}$ complexation, bi-DOPA hydrogen bonding, and aryloxyl radicalization (FIG. 1B).

Among the different types of Mfps, Mfp5 has the highest known level of DOPA (~26 mol %) and displays the highest adhesion strength (2.3-7 mJ $m^{-2}$), resulting in the design of various DOPA-based synthetic biomimetic materials. Moreover, other residues and sequence features may also play important roles in surface adhesion. For example, over half of the tyrosine residues in Mfp5 have neighboring lysine residues, which are believed to assist in priming surfaces for facile interaction with DOPA, indicating that Mfps employ a more complex mechanism than just using DOPA-based interactions. Fully understanding the sequence-structure-function relationship is ultimately key to designing better biomimetics, and recombinant Mfp5 is an attractive adhesive material for various applications, such as in surgical and medical glues and for underwater repair.

Recombinant Mfp5 has been previously expressed in E. coli. After enzymatic conversion of tyrosine residues to DOPA, the resulting protein displayed a surface adhesion force of 49 nN $\mu m^{-1}$ (force normalized to the radius of a contacting probe). Recently, Mfp5 was fused to the major subunit of curli protein CsgA, which exposed the Mfp5 domain on the exterior of self-assembled curli fibers. The β-sheet structure of the curli fiber contains intermolecular hydrogen bonds, enabling interactions between multiple fused Mfp5 domains. The resulting material displayed underwater surface adhesion forces up to 120 nN $\mu m^{-1}$. Covalent linking of multiple Mfp5 proteins at the proteins' termini also leads to strong underwater adhesives due to the increased probability of protein-surface interactions and the enhanced density of inter-protein interactions and entanglements, effectively reducing adhesion failure. As disclosed herein, a microbial-based approach has been developed to produce covalently linked Mfp5 oligomers to evaluate their underwater adhesion properties. Based on measurement, the high molecular weight Mfp oligomers (e.g., $Mfp5^3$) disclosed herein displayed higher underwater adhesivity than previous reports, and thus is more attractive as an adhesive and a coating material and has broader applications as described herein.

BRIEF DESCRIPTION OF THE DISCLOSURE

In one aspect, the present disclosure is directed a mussel foot protein (Mfp) comprising a full length polypeptide sequence from a mussel species, a partial polypeptide sequence from a mussel species, and combinations thereof.

In another aspect, the present disclosure is directed to a method for synthesizing a mussel foot protein (Mfp) oligomer protein, the method comprising: fusing an N-terminal split intein ($Int^N$) to a first Mfp repeat to produce a Mfp-$Int^N$ fusion protein; fusing a C-terminal split intein ($Int^C$) to a second Mfp repeat to produce an $Int^C$-Mfp fusion protein; and mixing the Mfp-$Int^N$ fusion protein and the $Int^C$-Mfp fusion protein to produce a Mfp oligomer protein.

In yet another aspect, the present disclosure is directed to a system for producing a mussel foot protein (Mfp) adhesive, the system comprising: a Mfp-$Int^N$ fusion protein; and an $Int^C$-Mfp fusion protein.

BRIEF DESCRIPTION OF THE DRAWINGS

The embodiments described herein may be better understood by referring to the following description in conjunction with the accompanying drawings.

FIG. 8A is an exemplary embodiment of a schematic of peak force tapping atomic force microscopy (PFT-AFM) experimental set-up in accordance with the present disclosure. FIG. 8B is an exemplary embodiment of representative approach/retract curves of Mfp$5^1_{DOPA}$ in accordance with the present disclosure. FIG. 8C is an exemplary embodiment of representative approach/retract curves of Mfp$5^2_{DOPA}$ in accordance with the present disclosure. FIG. 8D is an exemplary embodiment of representative approach/retract curves of Mfp$5^3_{DOPA}$ in accordance with the present disclosure.

DETAILED DESCRIPTION OF THE DISCLOSURE

Figure 1A:
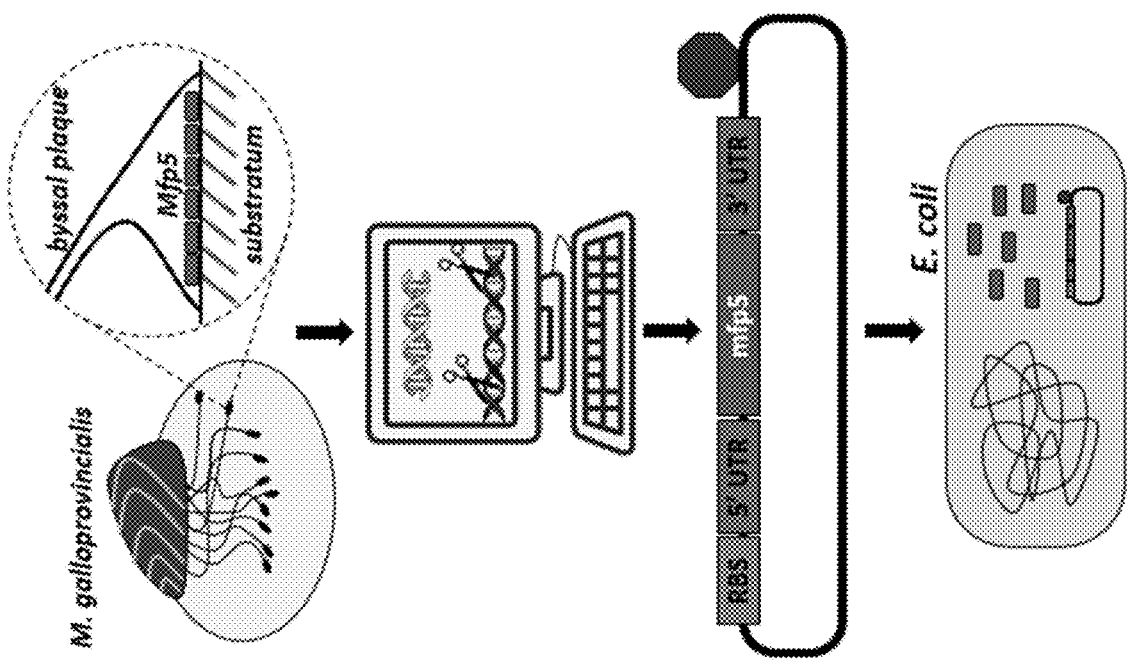
FIG. 1A is an exemplary embodiment of a schematic representation of the design and production of strong underwater adhesives using engineered microbes in accordance with the present disclosure.
Figure 1B:
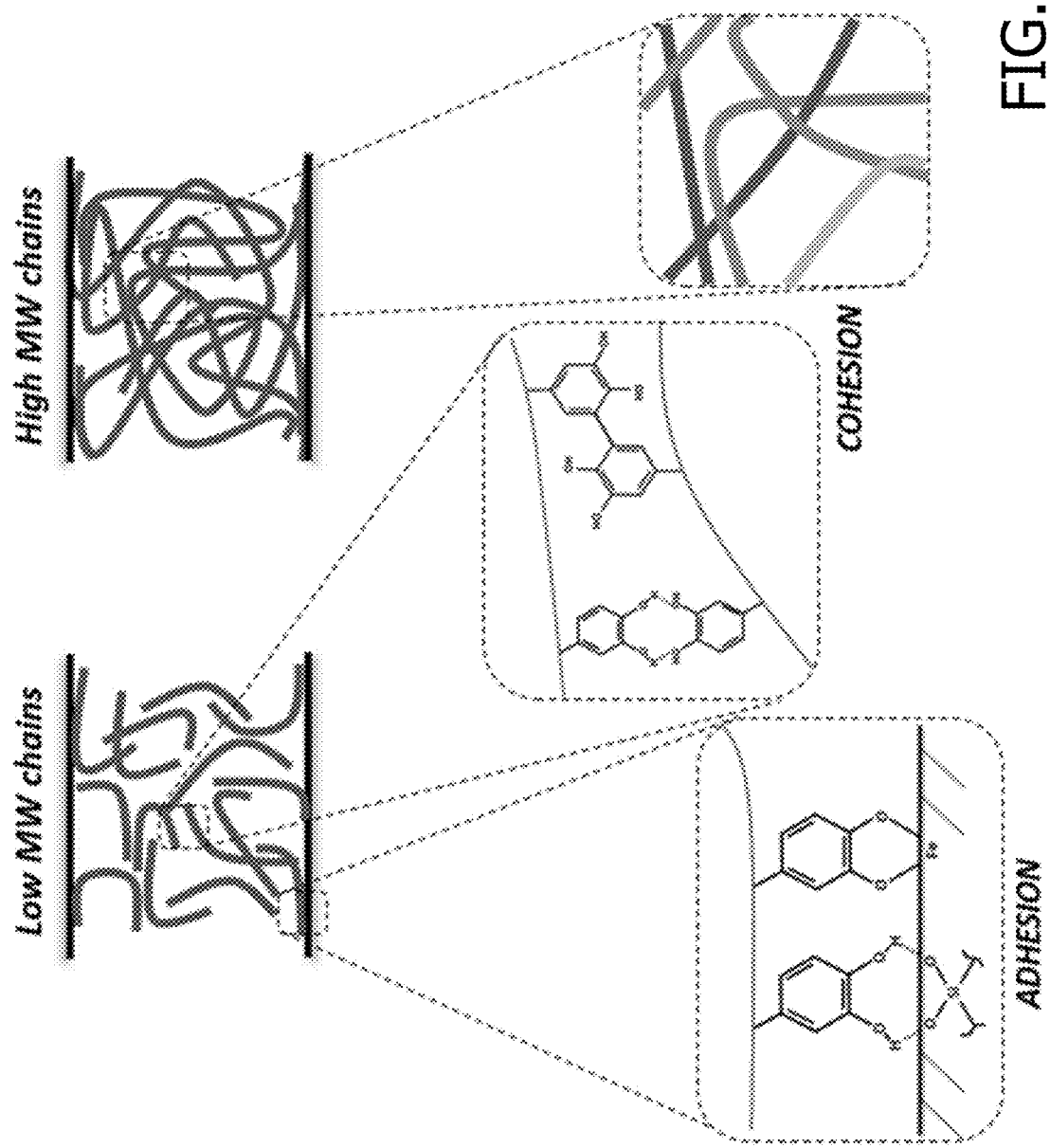
FIG. 1B is another exemplary embodiment of a schematic representation of the design and production of strong underwater adhesives using engineered microbes in accordance with the present disclosure.
Figure 1C:
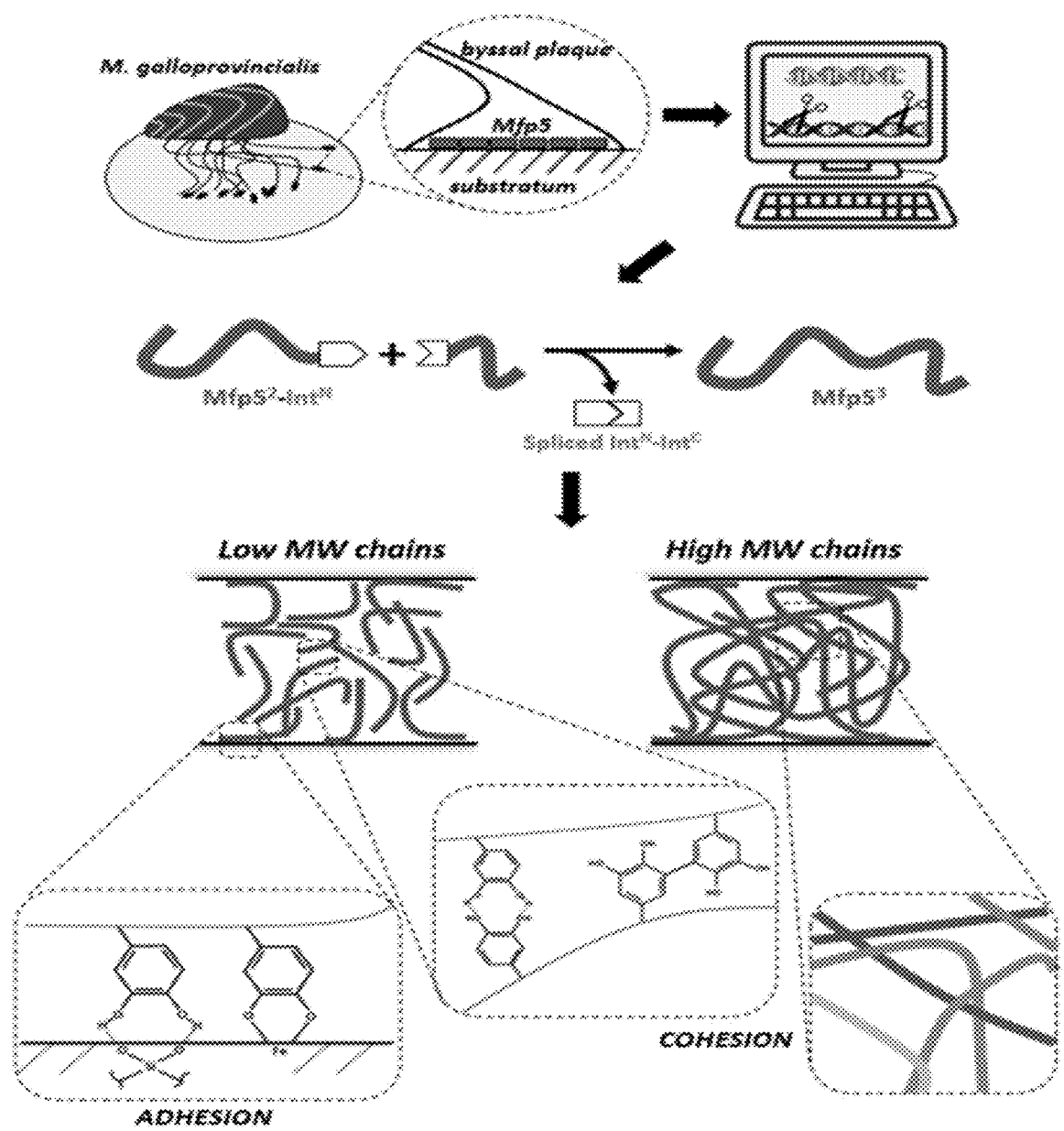
FIG. 1C is yet another exemplary embodiment of a schematic representation of the design and production of strong underwater adhesives using engineered microbes in accordance with the present disclosure.
Figure 2A:
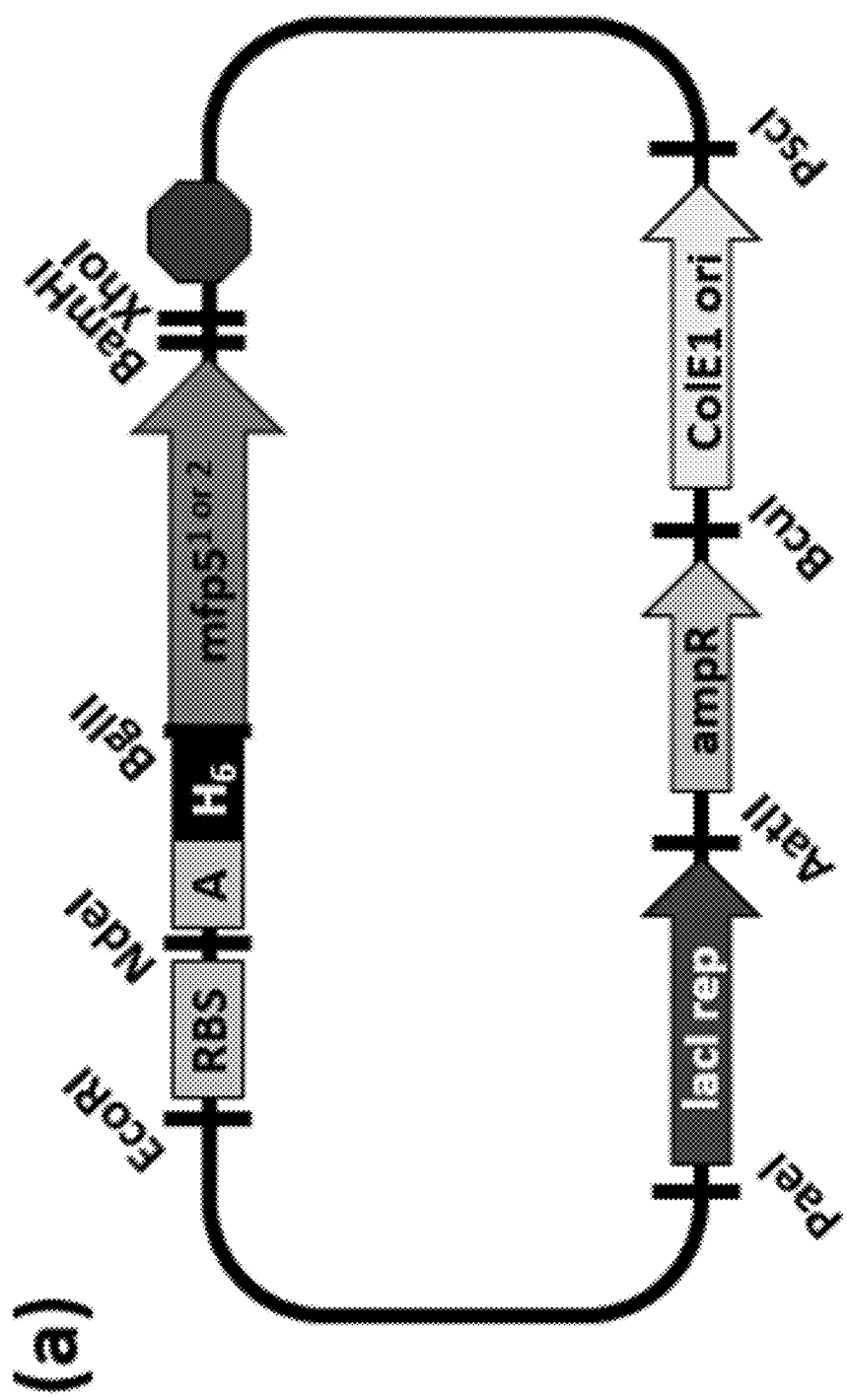
FIG. 2A is an exemplary embodiment of a BioBricks assembly system scheme that can be used for expressing a single gene along with an AKTK (SEQ ID NO: 19) expression tag and $H_6$ purification tag in accordance with the present disclosure.
Figure 2B:
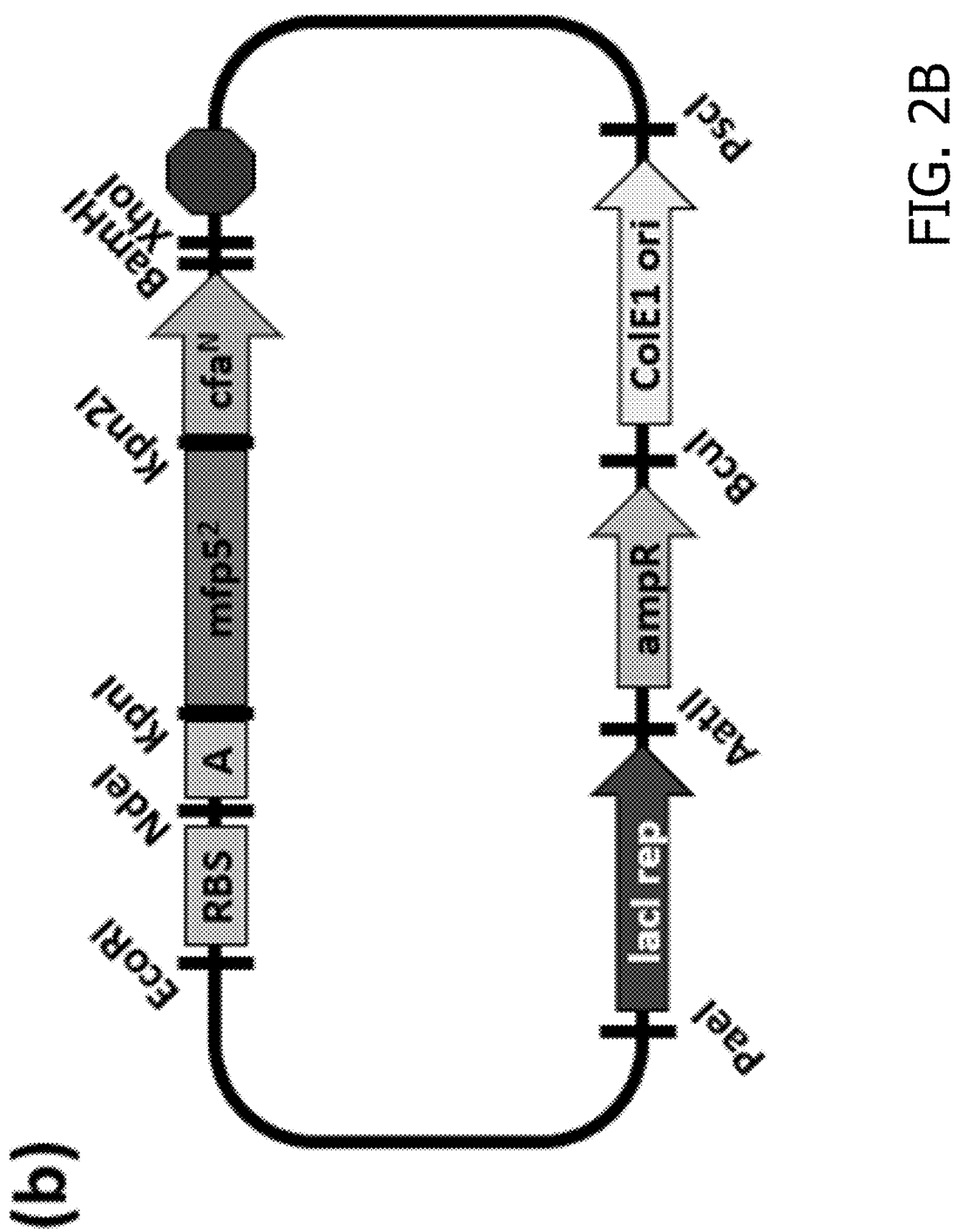
FIG. 2B is an exemplary embodiment of a BioBricks assembly system scheme that can be used for expressing a gene needing a C-terminal $Int^N$ Cfa fusion, along with an AKTK (SEQ ID NO: 19) expression tag in accordance with the present disclosure.
Figure 2C:
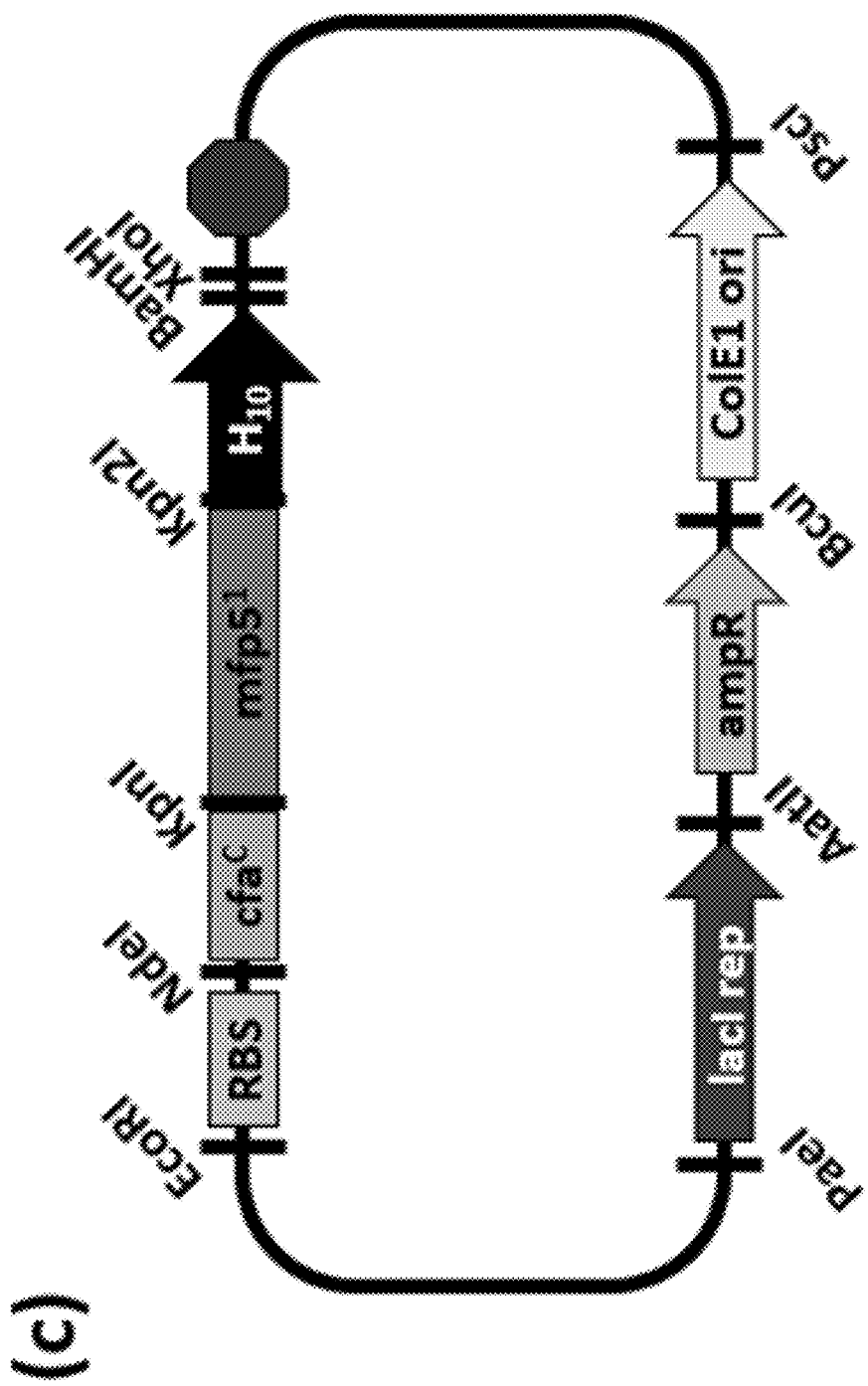
FIG. 2C is an exemplary embodiment of a BioBricks assembly system scheme that can be used for expressing a gene needing an N-terminal $Int^C$ Cfa fusion, along with an $H_{10}$ purification tag for post-ligation purification in accordance with the present disclosure.
Figure 3A:
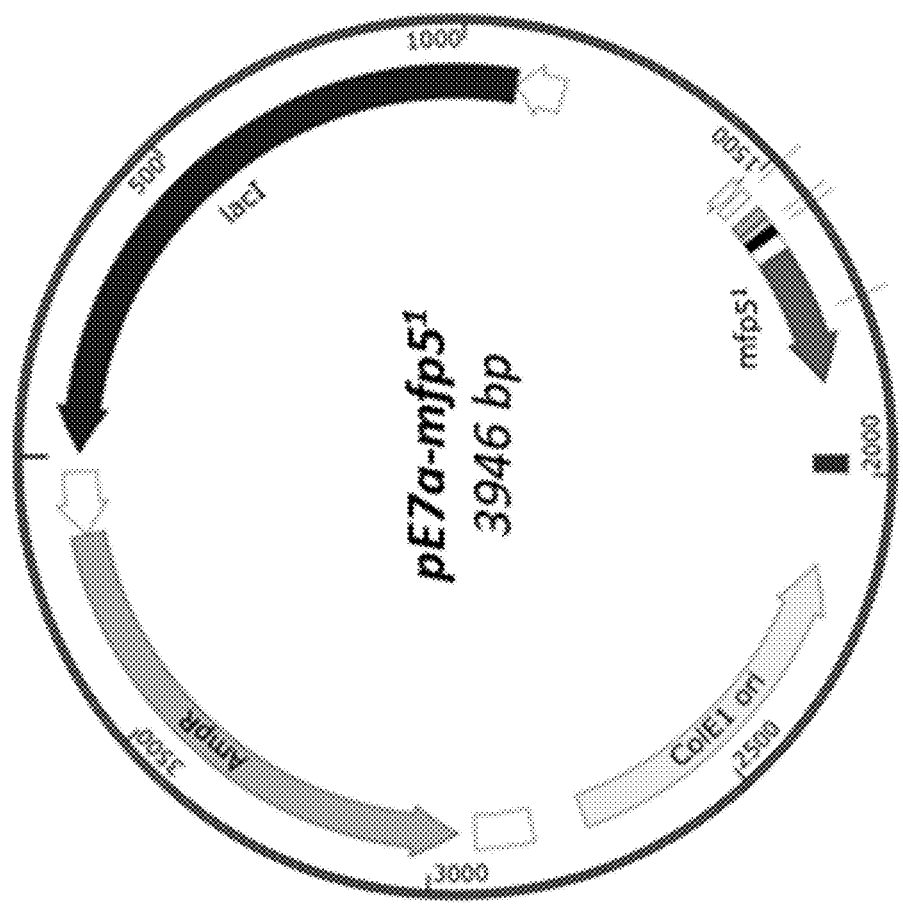
FIG. 3A is an exemplary embodiment of a plasmid map for pE7a-mfp$5^1$ in accordance with the present disclosure.
Figure 3B:
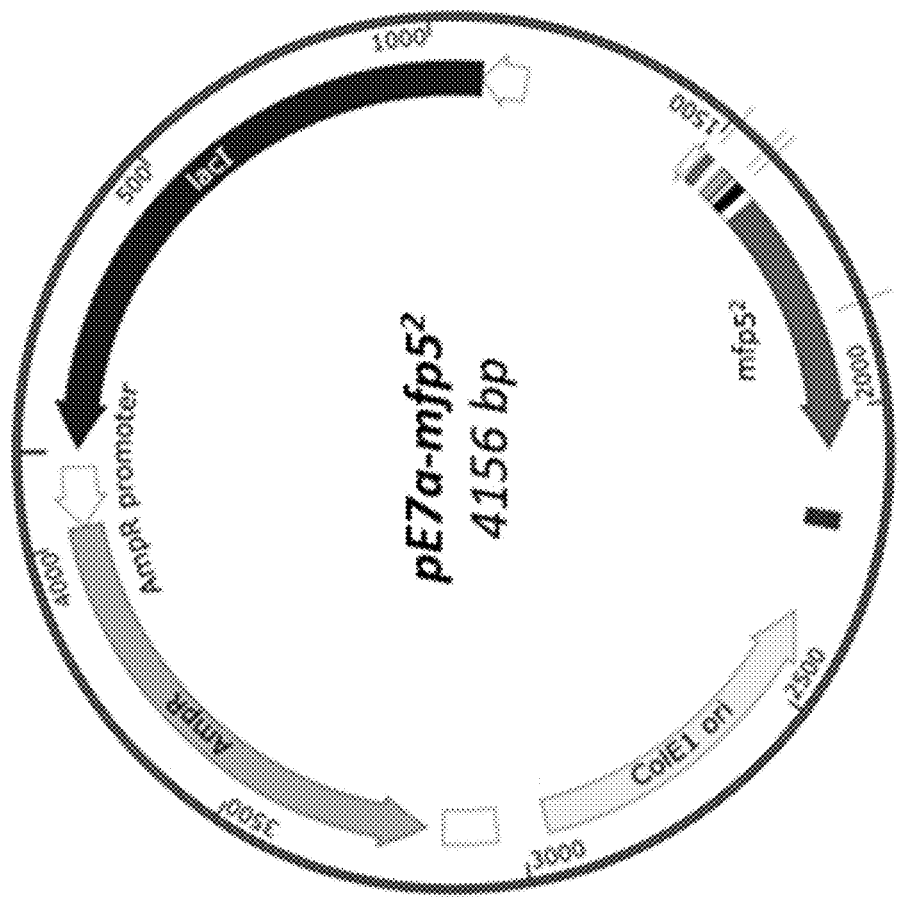
FIG. 3B is an exemplary embodiment of a plasmid map for pE7a-mfp$5^2$ in accordance with the present disclosure.
Figure 3C:
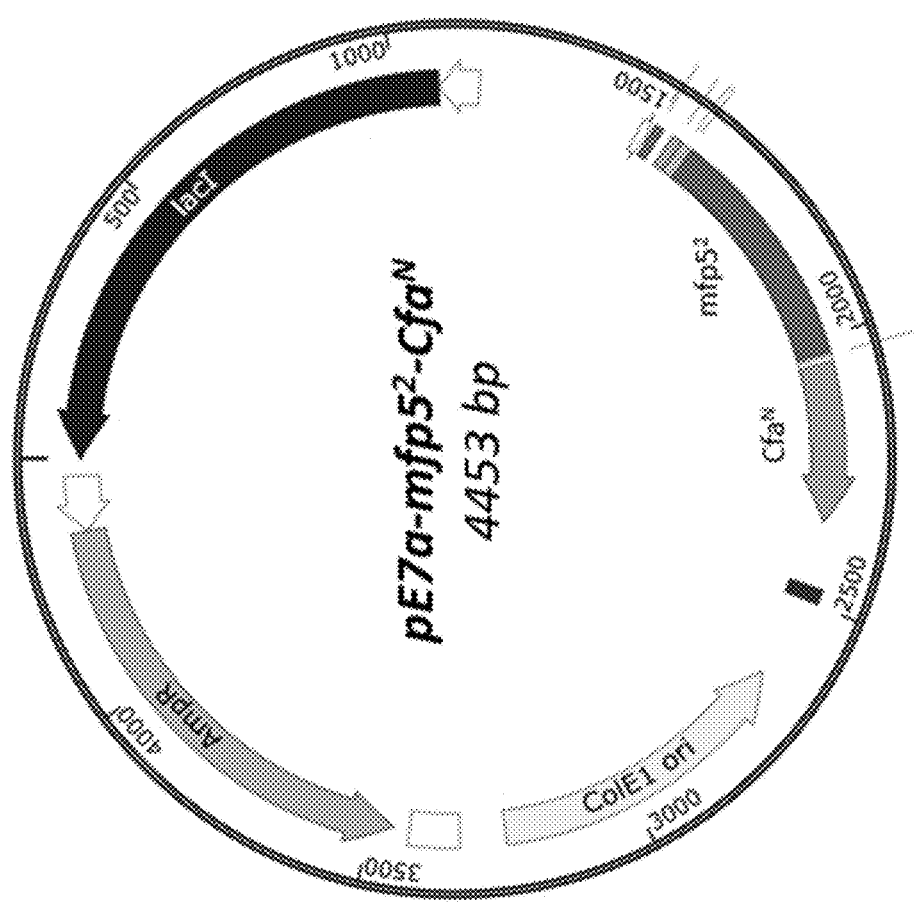
FIG. 3C is an exemplary embodiment of a plasmid map for pE7a-mfp$5^2$-Cfa$^N$ in accordance with the present disclosure.
Figure 3D:
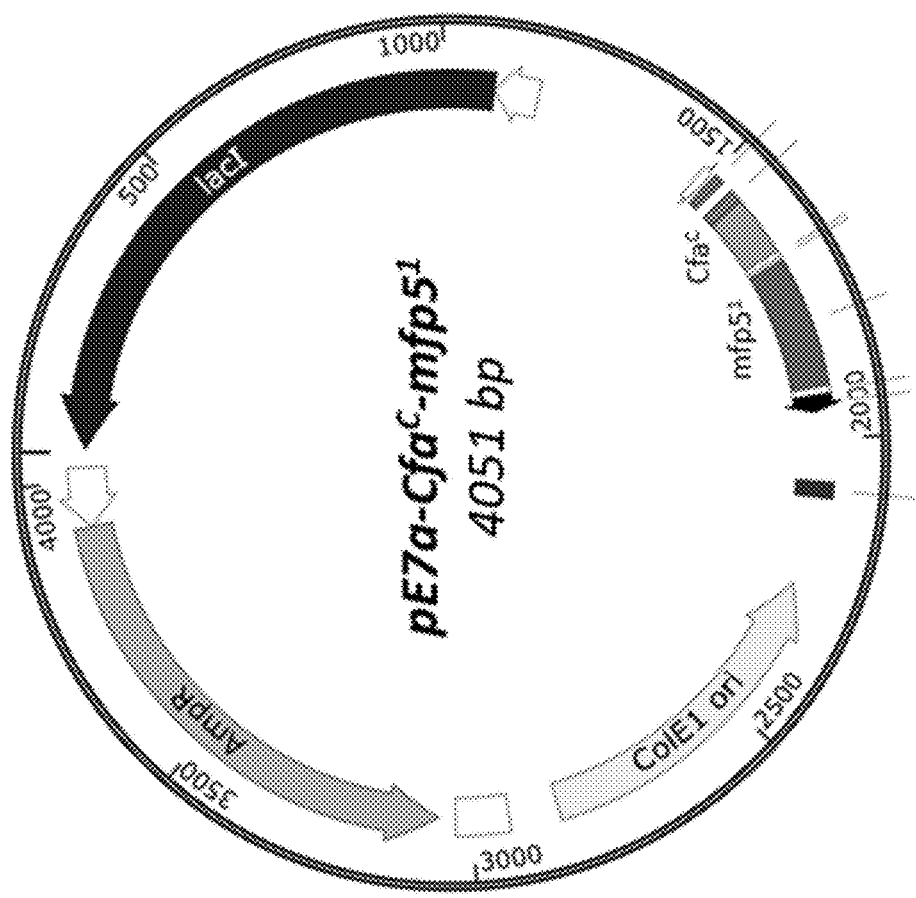
FIG. 3D is an exemplary embodiment of a plasmid map for pE7a-Cfa$^C$-mfp$5^1$ in accordance with the present disclosure.

Using synthetic DNA with codons optimized for *E. coli* expression, *Mytilus galloprovincialis* Mfp5 were designed together with Mfp5 oligomers containing two or three consecutive Mfp5 sequences (named Mfp5$^2$ and Mfp5$^3$) and cloned them into standardized expression vectors (FIGS. 2A-C and 3A-D). FIGS. 2A-C illustrate BioBricks assembly system schemes. This system allows for quick assembly of plasmids used in this study. All necessary parts for successful maintenance of plasmids and expression of proteins (repressors, antibiotic resistance, origins of replication, promoters, RBSs, terminators, split inteins, tags, and target genes) can be swapped in and out using the appropriate cut sites diagrammed above. The scheme shown in FIG. 2A can be used for expressing a single gene e.g. mfp5$^1$ or mfp5$^2$, along with an AKTK (SEQ ID NO: 19) expression tag and H$_6$ purification tag. The scheme shown in FIG. 2B can be used for expressing a gene needing a C-terminal Int$^N$ Cfa fusion, along with an AKTK (SEQ ID NO: 19) expression tag. The scheme shown in FIG. 2C can be used for expressing a gene needing an N-terminal Int$^C$ Cfa fusion, along with an H$_{10}$ purification tag for post-ligation purification. Plasmid maps for pE7a-mfp5$^1$, pE7a-mfp5$^1$, pE7a-mfp5$^2$-Cfa$^N$, and pE7a-Cfa$^C$-mfp5$^1$ are shown in FIGS. 3A-D, respectively. Unlabeled features are color-coded with the same scheme drawn out in FIGS. 2A-C.

Multiple Mfps from different mussel species exist, each having a slightly different amino acid sequence. In some embodiments, different Mfps (e.g., Mfp1, Mfp2, Mfp3, Mfp4, Mfp5, etc.) are utilized in the methods disclosed herein to produce Mfp oligomers with any number of repeats. Further, as described herein, a Mfp oligomer can be made from several different combinations via split intein reactions. For example, in some embodiments Mfp5$^3$ is made from Mfp5$^2$-Int$^N$ and Int$^C$-Mfp5$^1$. In other embodiments, Mfp5$^3$ is made from Mfp5$^1$-Int$^N$ and Int$^C$-Mfp5$^2$.

Figure 4:
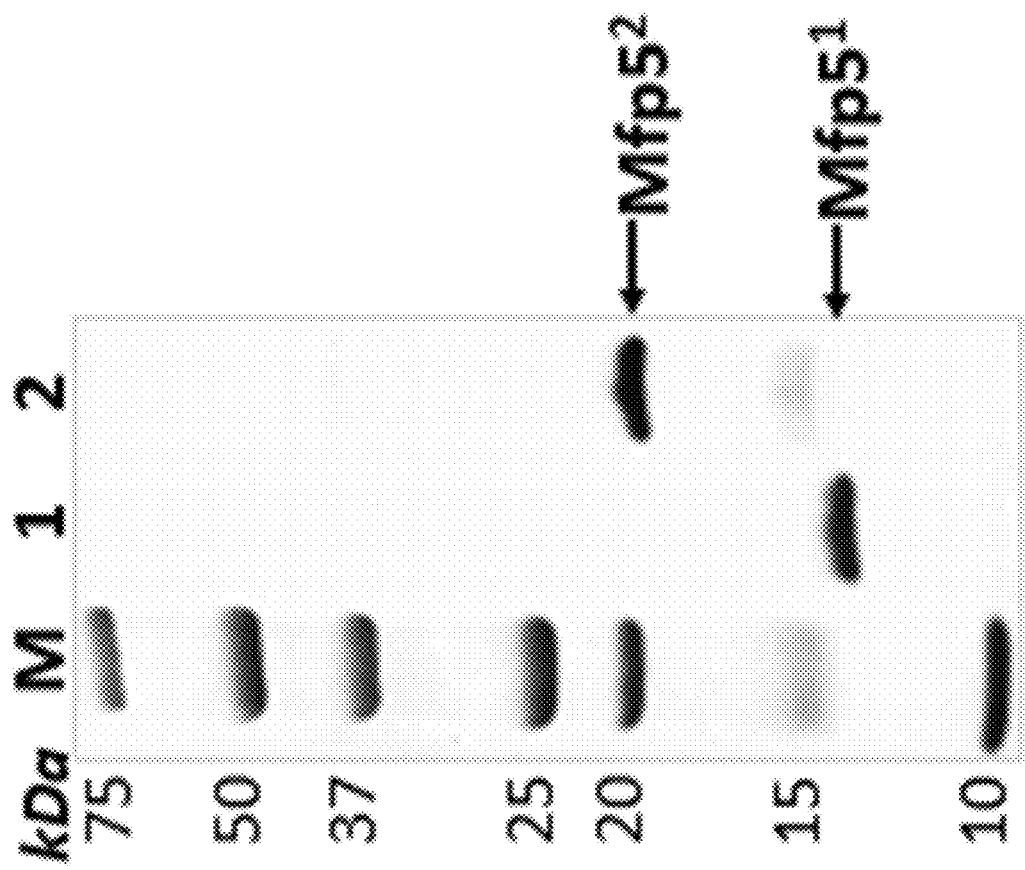
FIG. 4 is an exemplary embodiment of SDS-PAGE with Coomassie blue staining of purified Mfp$5^1$ and Mfp$5^2$ in accordance with the present disclosure.

In some embodiments, both Mfp5$^1$ and Mfp5$^2$ are produced in *E. coli* and purified using affinity chromatography to purities of 99.9% and 92.2%, respectively (FIG. 4). FIG. 4 shows SDS-PAGE with Coomassie blue staining of purified Mfp5$^1$ (Lane 1) and Mfp5$^2$ (Lane 2) with a protein marker standard (Lane M). However, Mfp5$^3$, designed using the same gene optimization algorithm, cannot be expressed under identical conditions. The lack of Mfp5$^3$ expression is likely caused by a combination of the repetitive nature of the coding sequence, translation inhibition by complex mRNA secondary structures, and a high demand for tyrosyl tRNA. Consequently, and as disclosed herein, split inteins (SI) were utilized to ligate separately expressed Mfp5$^1$ and Mfp5$^2$ to yield the Mfp5$^3$ protein.

Figure 5A:
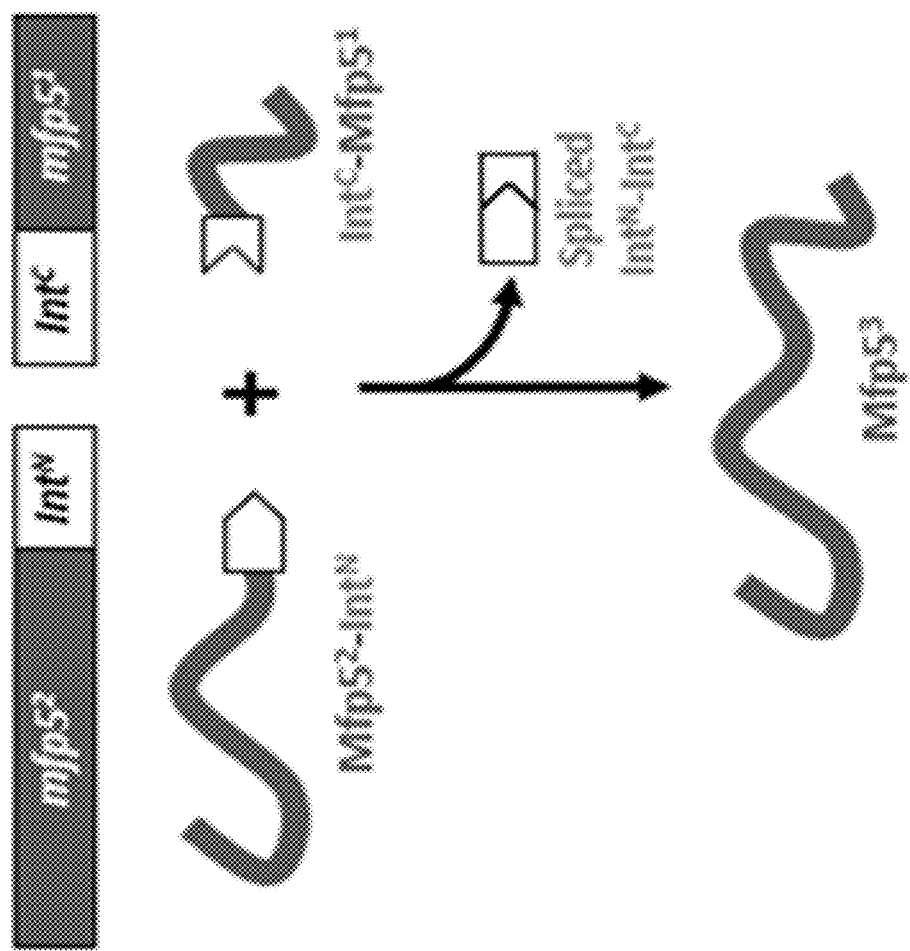
FIG. 5A is an exemplary embodiment of a schematic of gene constructs and the split-intein mediated ligation process of Mfp$5^2$-$Int^N$ and $Int^C$-Mfp$5^1$ for the production of Mfp$5^3$ in accordance with the present disclosure.
Figure 5B:
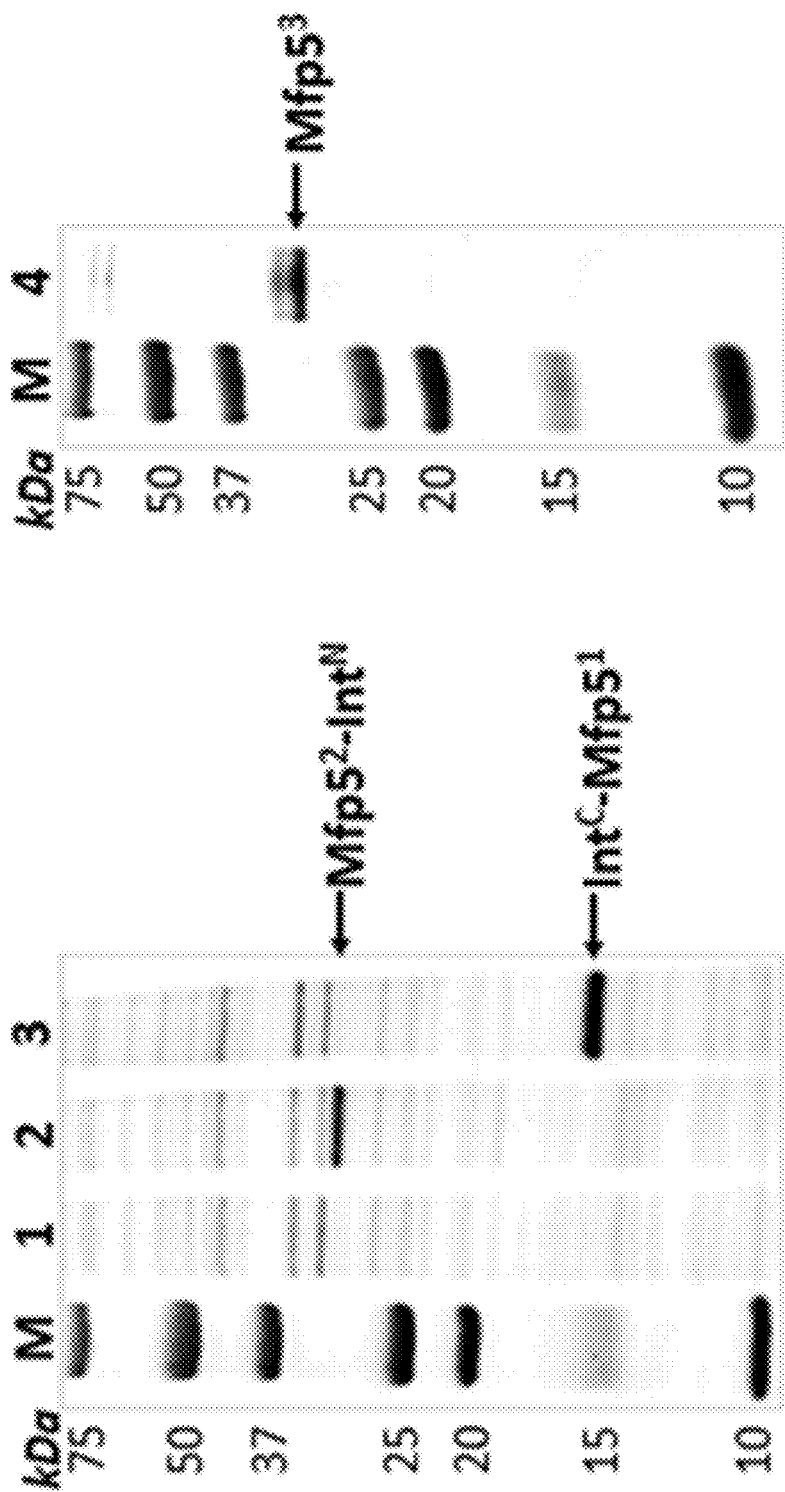
FIG. 5B is an exemplary embodiment of SDS-PAGE with Coomassie blue staining of split intein fused Mfp5 reactants and purified Mfp$5^3$ product in accordance with the present disclosure.

SIs are auto-catalytic peptides that catalyze the spontaneous splicing-ligation reactions between two SI-fused target proteins, assembling the two target proteins covalently in trans (FIG. 5A). FIG. 5A shows a schematic of gene constructs and the split-intein mediated ligation process of Mfp5$^2$-Int$^N$ and Int$^C$-Mfp5$^1$ for the production of Mfp5$^3$. An engineered Cfa SI was employed due to its rapid protein splicing rate in denaturing conditions (e.g., 8 M urea), which were used to efficiently extract and solubilize the target Mfp5 proteins. In some embodiments, a different SI (such as any known suitable SI) can be used. The N-terminal split intein (Int$^N$) and C-terminal split intein (Int$\alpha$) were genetically fused to Mfp5$^2$ and Mfp5$^1$, respectively, resulting in two fusion proteins, Mfp5$^2$-Int$^N$ and Int$^C$-Mfp5$^1$. These fusion proteins in whole cell lysate mixtures were then mixed, yielding Mfp5$^3$, which was further purified from the nonspecific proteins, the spliced SI complex, and the unreacted low molecular weight proteins to 96.4% purity (FIG. 5B). FIG. 5B shows SDS-PAGE with Coomassie blue staining of split intein fused Mfp5 reactants (lanes 2 and 3) and purified Mfp5$^3$ product (lane 4) with a protein marker standard (lane M). Lane 1 contains the whole cell lysate of wild type *E. coli* that does not express target protein. Purified proteins were then reacted with tyrosinase to convert tyrosine to DOPA, yielding modified proteins, named Mfp5$^1_{DOPA}$, Mfp5$^2_{DOPA}$, and Mfp5$^3_{DOPA}$. Matrix-assisted laser desorption/ionization-time of flight mass spectrometry (MALDI-TOF MS) analysis showed an average tyrosine modification rate of 65% under conditions described herein (FIGS. 6A-B and 7A-B), consistent with previous modification efficiencies from similar methods.

Figure 6A:
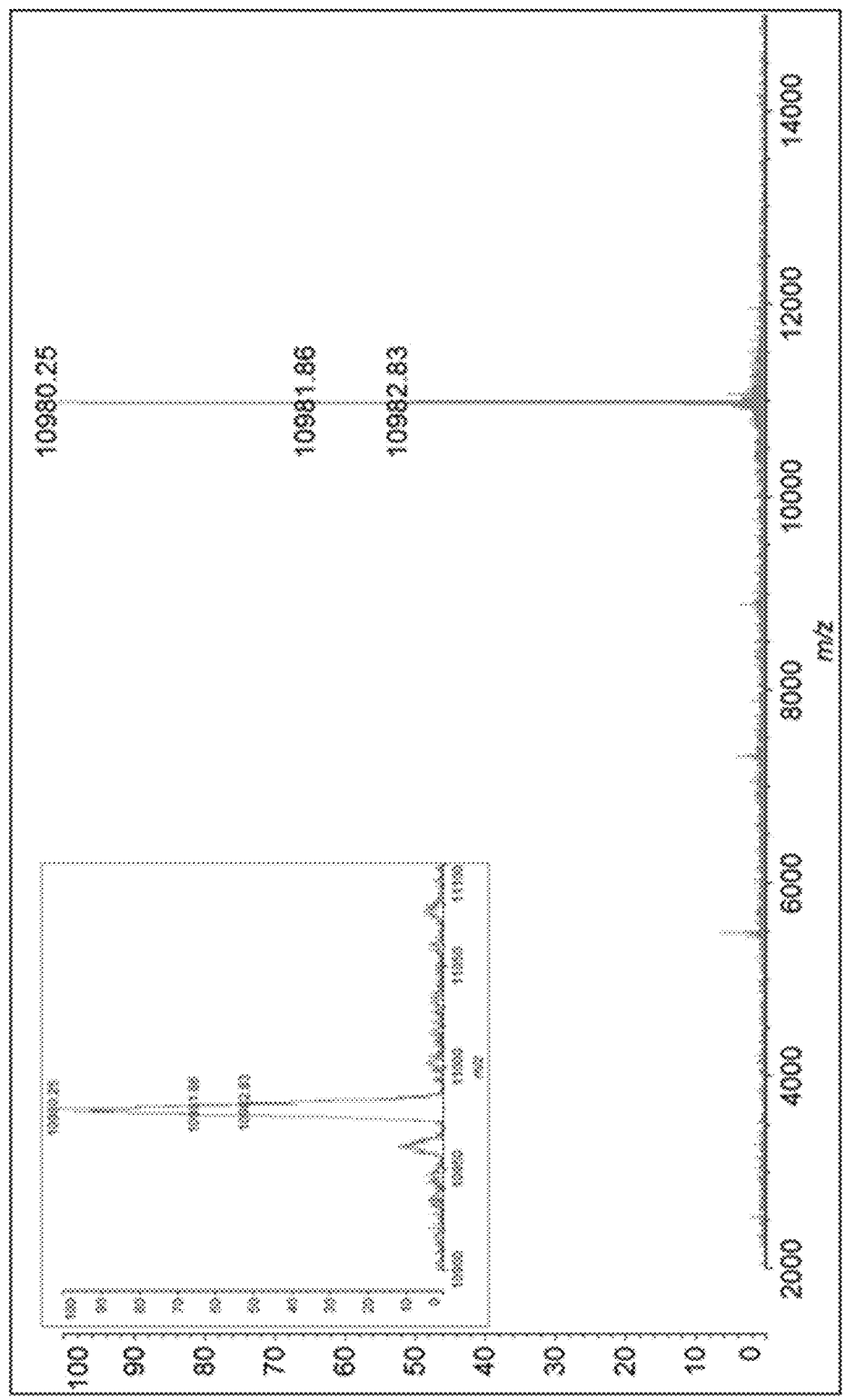
FIG. 6A is an exemplary embodiment of a MALDI-TOF spectrum of unmodified Mfp$5^1$ in accordance with the present disclosure.
Figure 6B:
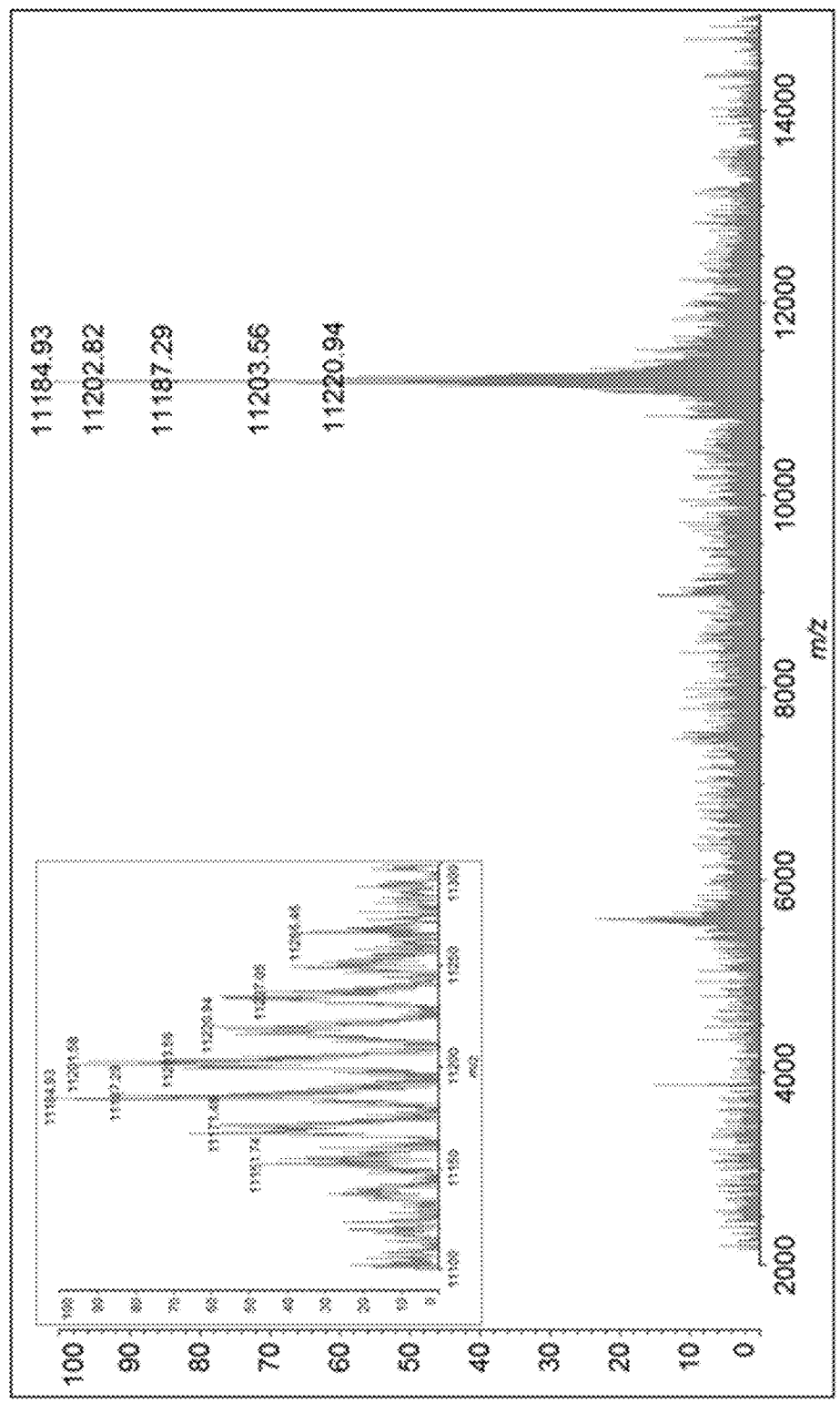
FIG. 6B is an exemplary embodiment of a MALDI-TOF spectrum of Mfp$5^1_{DOPA}$ in accordance with the present disclosure.

MALDI-TOF spectra of unmodified Mfp5$^1$ and Mfp5$^1_{DOPA}$ are shown in FIGS. 6A and 6B, respectively. The unmodified Mfp5$^1$ had an expected molecular weight of 10978.02 Da. After modification of tyrosine to DOPA, the mass increased. Insets show a zoomed-in view of the dominant single-charged (1+) peak. When protein was modified, there was a collection of peaks (roughly 16 Da apart from one another from the removal of an oxygen atom), representing varying numbers of modifications ranging from 11 to 18 out of 20 available modification sites, with the largest peak showing a mass of 11184.93 Da, representing an average modification yield of 65%.

Figure 7A:
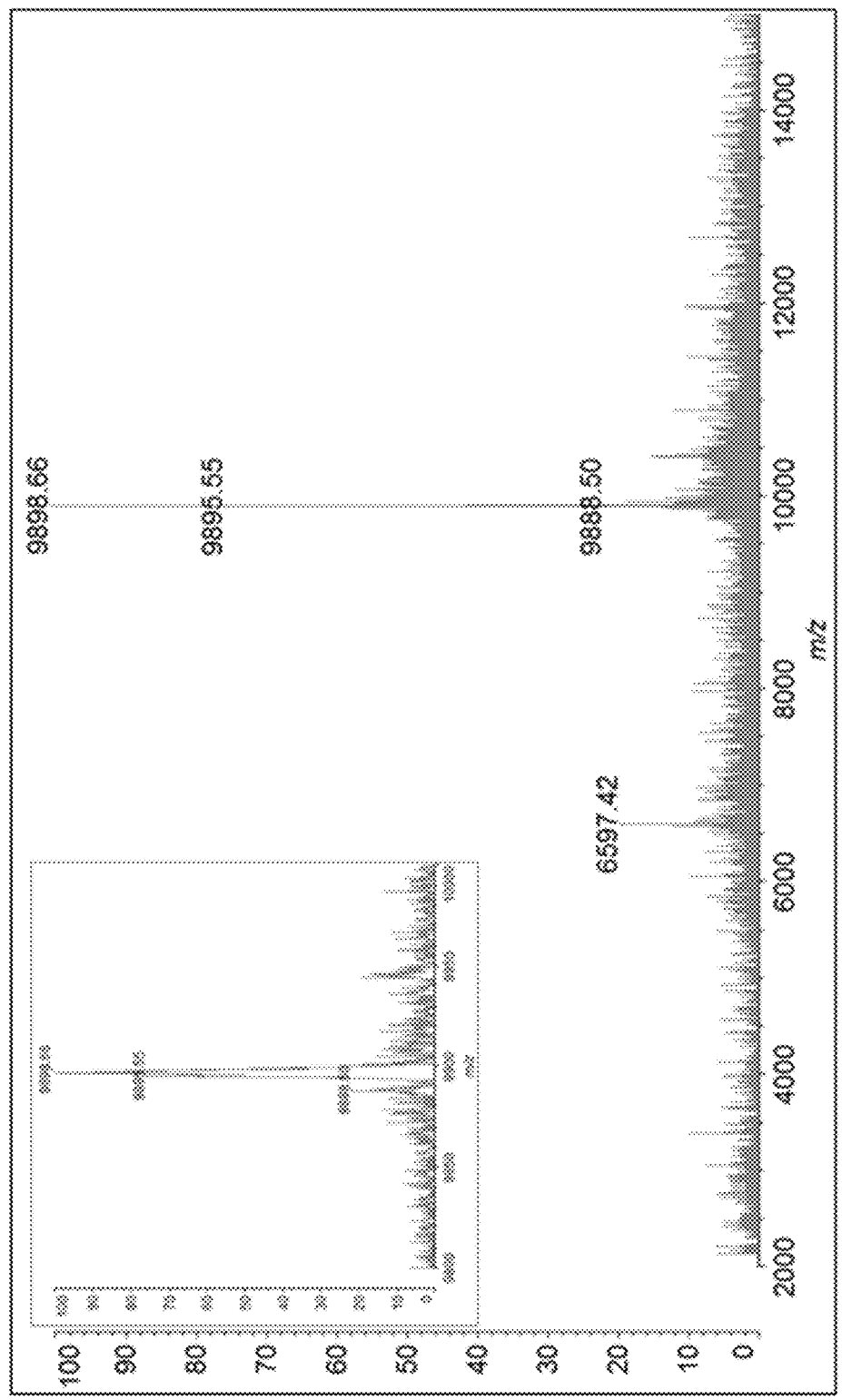
FIG. 7A is an exemplary embodiment of a MALDI-TOF spectrum of unmodified Mfp$5^2$ in accordance with the present disclosure.
Figure 7B:
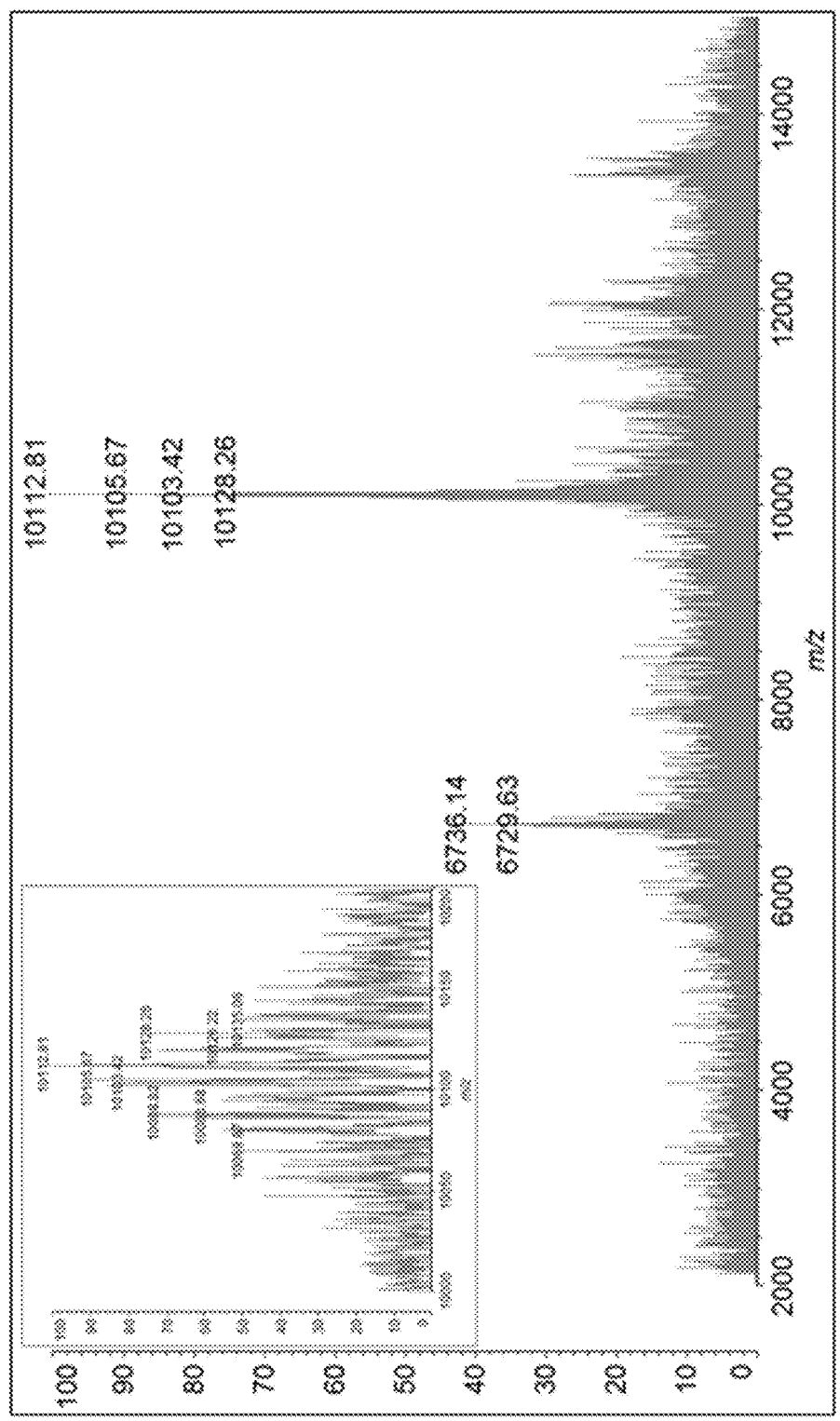
FIG. 7B is an exemplary embodiment of a MALDI-TOF spectrum of Mfp$5^2_{DOPA}$ in accordance with the present disclosure.

MALDI-TOF spectra of unmodified Mfp5$^2$ and Mfp5$^2_{DOPA}$ are shown in FIGS. 7A and 7B, respectively. The unmodified Mfp5$^2$ had an expected molecular weight of 19793.86 Da. After modification of tyrosine to DOPA, the mass increased. Insets show a zoomed-in view of the dominant double-charged (2+) peak. When protein was modified, there was a collection of peaks (roughly 8 Da apart from one another, which is half the size of the removed oxygen atom), representing varying numbers of modifications ranging from 11 to 18 out of 20 available modification sites, with the largest peak showing a mass of 11184.93, representing an average modification yield of 65%.

Peak force tapping atomic force microscopy (PFT-AFM) was used to examine asymmetric adhesive and cohesive characteristics of the Mfp5 proteins between a colloidal probe and a protein-adsorbed mica surface under aqueous conditions (see FIG. 8A). FIG. 8A shows a schematic of the peak force tapping atomic force microscopy (PFT-AFM) experimental set-up. The colloidal probe was moved toward the protein layer (probe approach) and then "cured" for various times before the probe was retracted from the surface (probe retraction). As FIG. 8A illustrates, the cantilever with a colloidal probe (1) approaches the surface of the sample deposited on mica and (2) interacts with oligomer chains with varying cure times. The probe then begins to (3) retract from the sample and protein-surface, and protein-probe interactions start to break. Applying longer separation distances (4) causes protein-protein interactions to break further until the probe is completely separated from the mica surface. For all tested protein samples, approach-retract curves were collected on several days from multiple sample locations and for multiple cure times at each sample location (FIG. 8B-D). The representative approach/retract curves of Mfp5$^1_{DOPA}$ (FIG. 8B), Mfp5$^2_{DOPA}$ (FIG. 8C), and Mfp5$^3_{DOPA}$ (FIG. 8D) each had a cure time of 10 seconds and were collected on multiple days at multiple sample locations. Triplicate measurements were taken at individual locations shown in the same color. $Z_{rel}$ represents the separation distance between surfaces relative to the points of maximum contact (positive adhesion force).

Figure 9B:
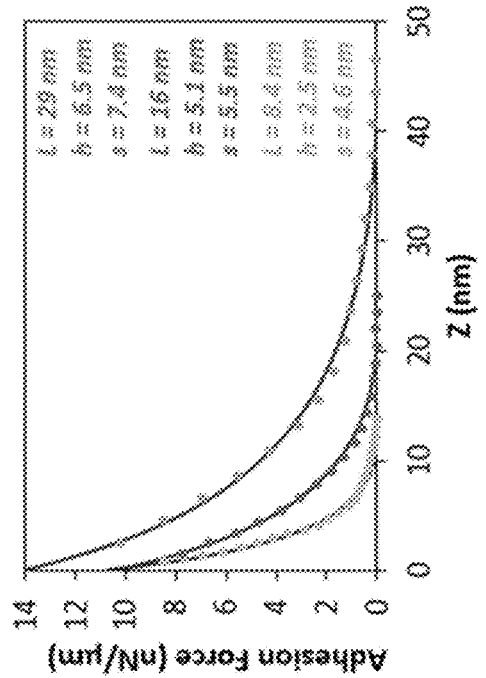
FIG. 9B is an exemplary embodiment of fitting of representative approach curves to the Alexander de Gennes (AdG) model (red solid lines) in accordance with the present disclosure.
Figure 9A:
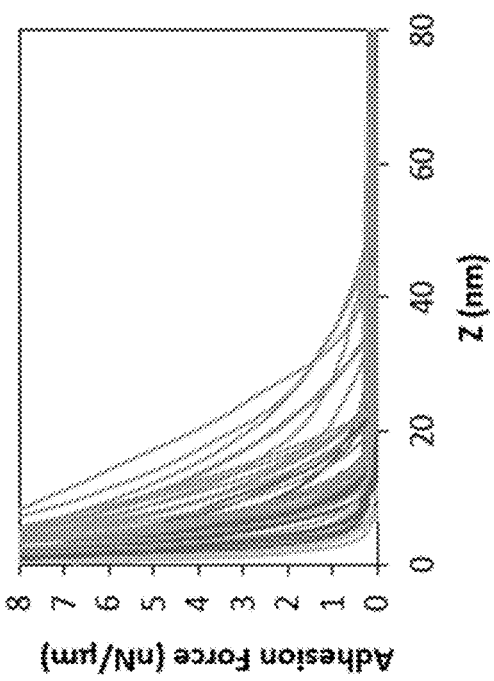
FIG. 9A is an exemplary embodiment of positive approach curves for Mfp$5^1_{DOPA}$ (yellow), Mfp$5^2_{DOPA}$ (blue), and Mfp$5^3_{DOPA}$ (green) showing repulsive interactions during probe approaching in accordance with the present disclosure.
Figure 9C:
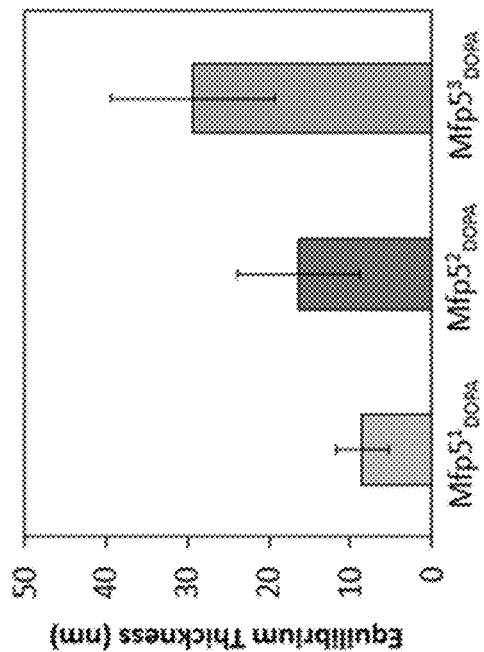
FIG. 9C is an exemplary embodiment of average equilibrium thicknesses of the three modified Mfps in accordance with the present disclosure.

FIGS. 9A and 9B show approach curves of DOPA-modified Mfps. For all three Mfp5 proteins, no negative adhesion force was observed during probe approach, indicating that the interaction was dominated by repulsive interactions under the experimental conditions (FIG. 9A). FIG. 9A shows positive approach curves for $Mfp5^1_{DOPA}$ (yellow), $Mfp5^2_{DOPA}$ (blue), and $Mfp5^3_{DOPA}$ (green) showing repulsive interactions during probe approaching. The approach curves were fitted to the Alexander-de Gennes (AdG) model (described herein below), which was employed to describe the physisorption of intrinsically disordered gelatin coils, polymer layers, and other proteins to colloidal probes. Fitted results indicate apparent average protein-layer equilibrium thicknesses (L) of approximately 8.5, 16, and 29 nm for $Mfp5^1_{DOPA}$, $Mfp5^2_{DOPA}$, and $Mfp5^3_{DOPA}$, respectively (FIG. 9B). FIG. 9B shows fitting of representative approach curves to the AdG model (red solid lines). These values are greater than the estimated radii of gyration of each of these proteins (3.1, 4.4, and 5.5 nm for $Mfp5^1_{DOPA}$, $Mfp5^2_{DOPA}$, and $Mfp5^3_{DOPA}$, respectively) when adopting random coil structures. These greater lengths indicate that a protein multilayer is present and that with increasing molecular weight, there is an increase in the amount of protein adsorbed on the surface. FIG. 9C shows average equilibrium thicknesses of the three modified Mfps. The average thickness of each protein was obtained from at least 18 fittings. Error bars represent standard deviations (n≥18). Accordingly, high molecular weight increases inter-protein interactions and/or entanglements, leading to thicker protein layers (FIG. 9C).

Figure 10A:
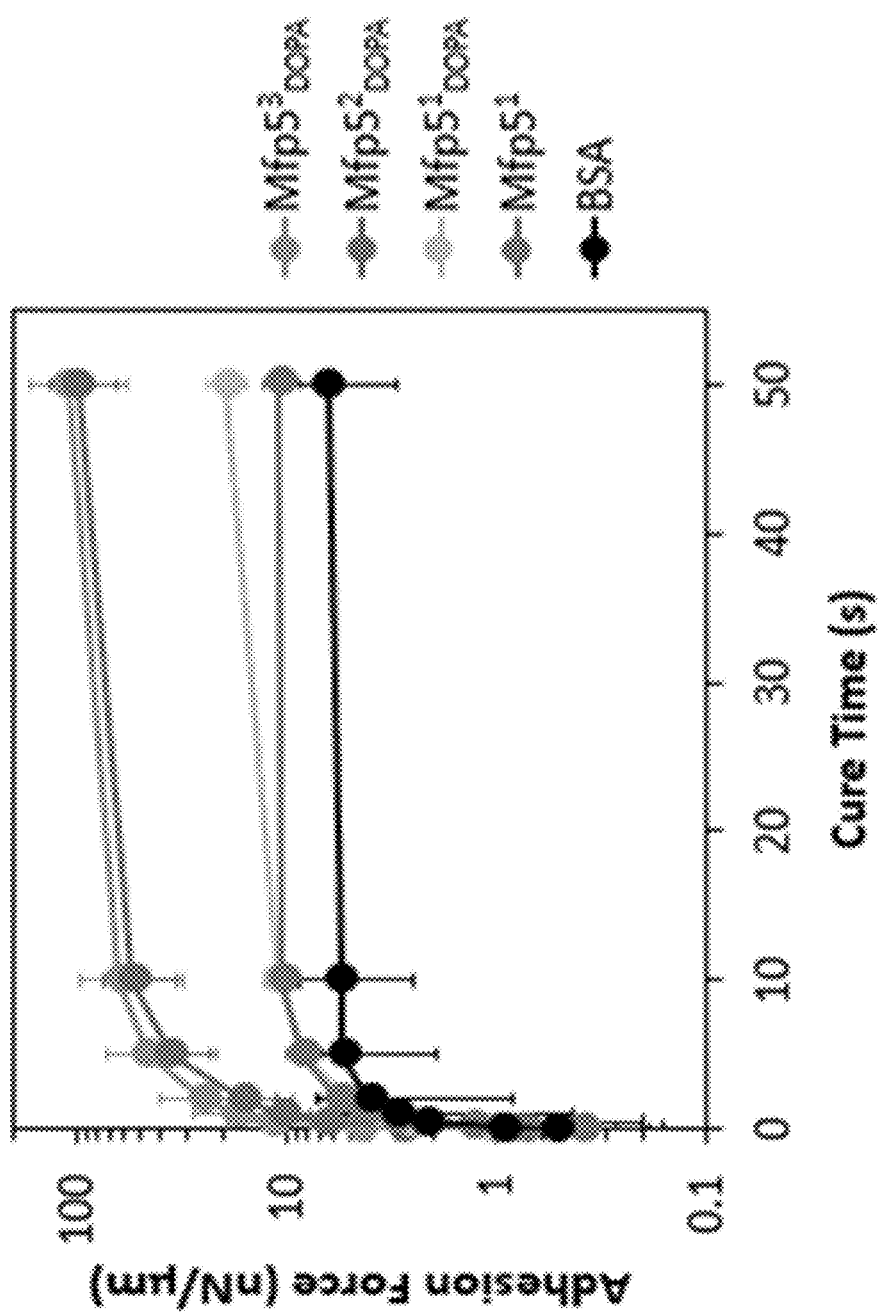
FIG. 10A is an exemplary embodiment of adhesion force versus probe cure time in accordance with the present disclosure.
Figure 10B:
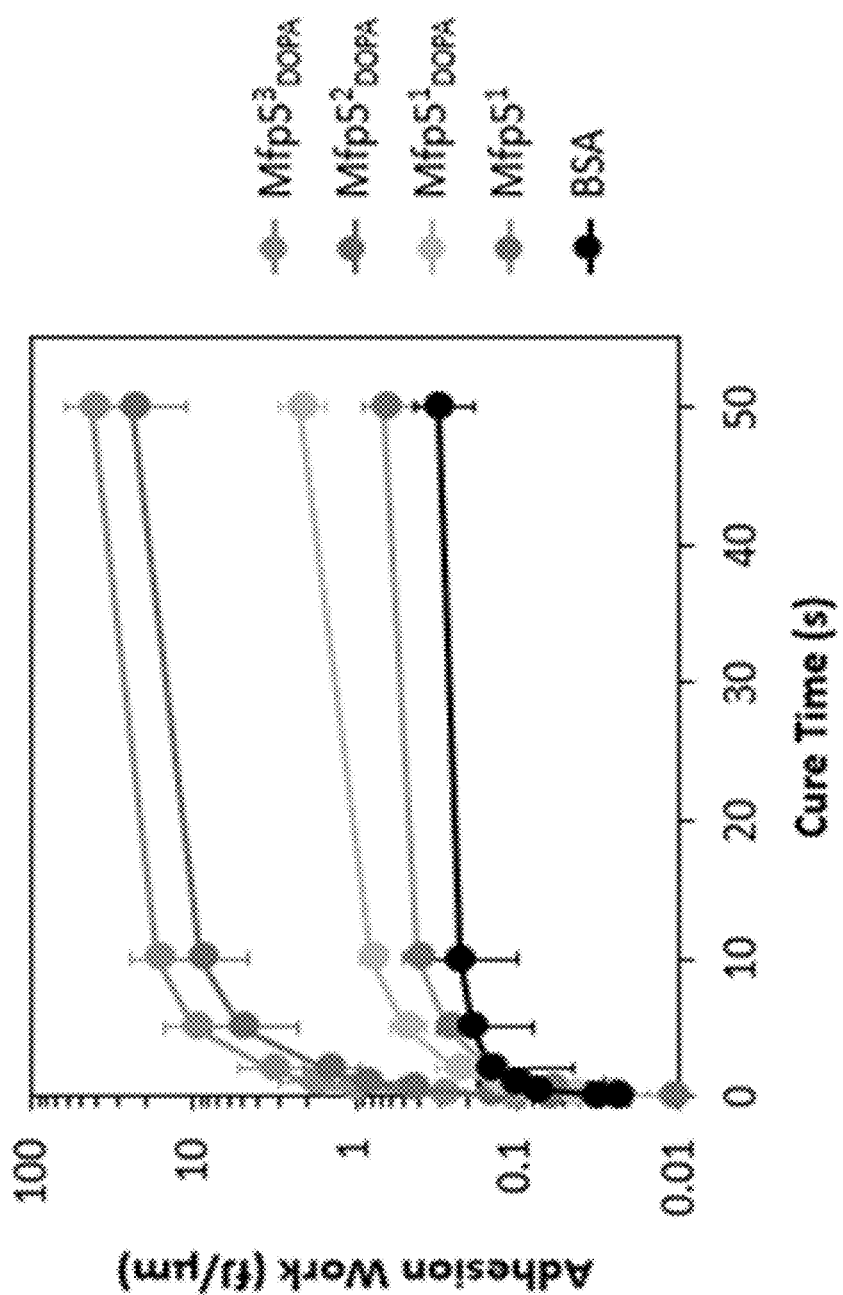
FIG. 10B is an exemplary embodiment of adhesion work versus probe cure time in accordance with the present disclosure.

FIGS. 10A and 10B show adhesion force and adhesion work, respectively. Protein adhesion force was calculated from the maximum attraction force of the retract curves and were normalized by the radius of the colloidal probe. All proteins displayed a cure time-dependent adhesion, with increasing adhesion force after longer curing times (FIG. 10A). In FIG. 10A, the adhesion force versus probe cure time is shown for BSA (black), $Mfp5^1$ (grey) $Mfp5^1_{DOPA}$ (yellow), $Mfp5^2_{DOPA}$ (blue), and $Mfp5^3_{DOPA}$ (green). Error bars represent standard deviations (n≥21). For all cure times, bovine serum albumin (BSA) and unmodified $Mfp5^1$ exhibited little adhesion (<11 nN Adhesion forces of $Mfp5^1_{DOPA}$ were similar to those of unmodified $Mfp5^1$ at cure times of less than 10 s, but became 1.8-fold higher at 50 s cure times (FIG. 10A). This behavior indicates that there is a required minimum time for DOPA-mediated interactions to dominate over non-catechol interactions between protein molecules and the two contact surfaces under the experimental conditions. At a cure time of 50 s, the adhesion forces of $Mfp5^2_{DOPA}$ and $Mfp5^3_{DOPA}$ were 5.1- and 5.7-fold higher than that of $Mfp5^1_{DOPA}$, respectively, indicating a positive correlation between adhesion force with protein chain-length (FIG. 10A).

Figure 11:
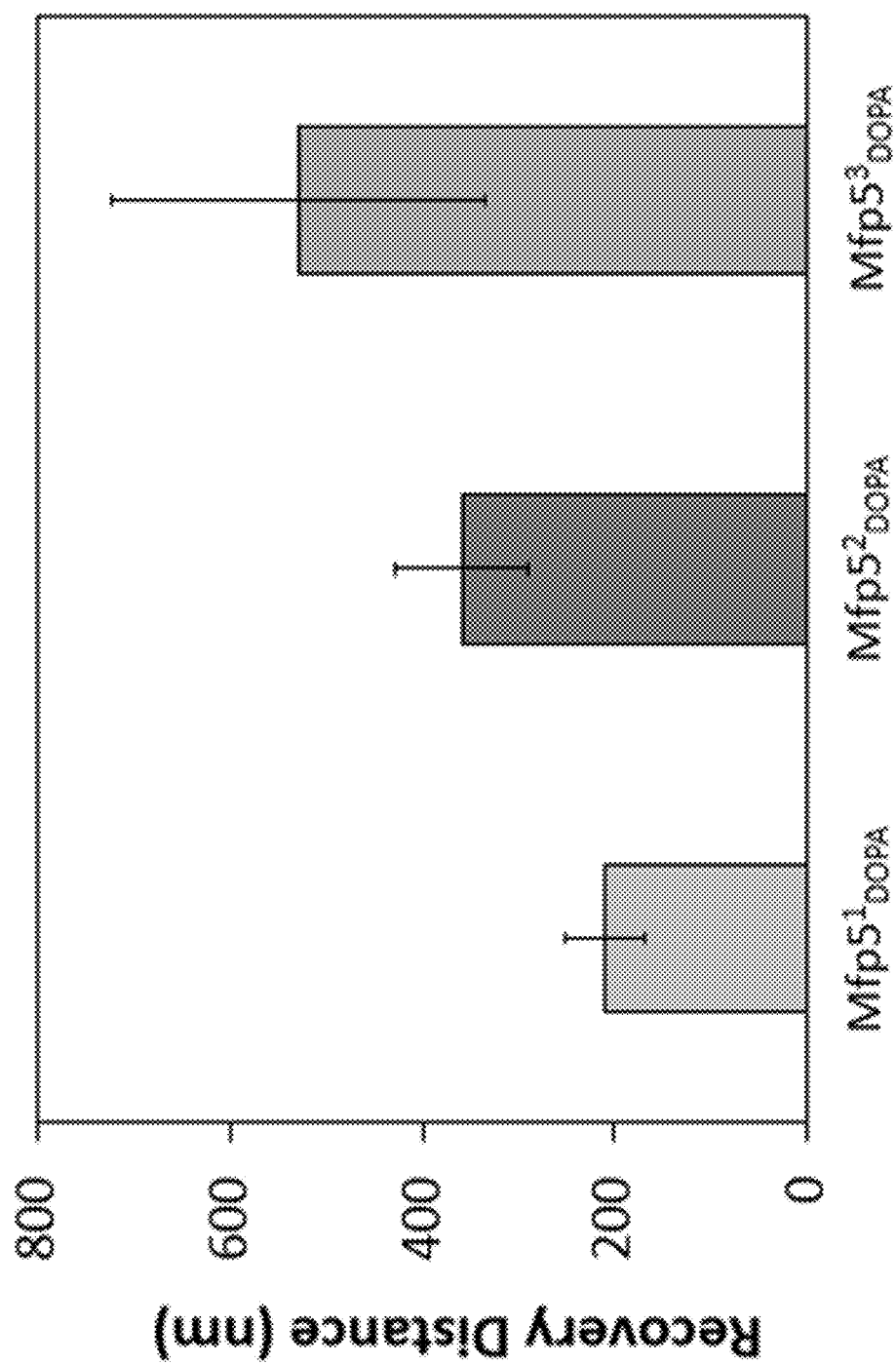
FIG. 11 is an exemplary embodiment of recovery distance in accordance with the present disclosure.

A similar positive correlation was also observed using synthetic poly-dihydroxystyrene-co-styrene polymers. From the retract curves, the recovery distance was also measured, which is defined as the length between the point where maximum adhesion force is achieved and the point where the probe is re-established to the initial zero adhesion baseline. FIG. 11 shows recovery distance, calculated as the distance between the point of initial oligomer fracture (separation distance at point of maximum adhesion force) and the point at which probe has been fully separated at cure times of 50 s. Error bars represent standard deviations (n≥8). At a cure time of 50 s, the recovery distance of $Mfp5^1_{DOPA}$ is 210 nm (FIG. 11), which is approximately 25-fold longer than the thickness of an $Mfp5^1_{DOPA}$ protein layer (8.5 nm, FIG. 9C) and 6-fold longer than the estimated length of a single fully extended, 97-residue $Mfp5^1$DOPA protein chain (34 nm). The long recovery distance indicates that multiple protein chains must interact with each other before complete detachment of the probe from the mica surface, reflected by the observations of multiple and discrete adhesion events in single retract curves in our results. Cohesive interactions may play a major role during surface adhesion. The average recovery distances of $Mfp5^2_{DOPA}$ and $Mfp5^3_{DOPA}$ were 1.7- and 2.5-fold longer than that of $Mfp5^1_{DOPA}$, respectively, suggesting more extensive inter-chain interactions with increasing molecular weight.

Related to recovery distance, another critical material property for adhesives is adhesion work, also known as peel force or work of separation. In FIG. 10B, the adhesion work versus probe cure time is shown for BSA (black), $Mfp5^1$ (grey) $Mfp5^1_{DOPA}$ (yellow), $Mfp5^2_{DOPA}$ (blue), and $Mfp5^3_{DOPA}$ (green). Error bars represent standard deviations (n≥21). Adhesion work is directly correlated with energy dissipation. A material with high adhesion work dissipates mechanical energy efficiently and reduces adhesion failure when a crack in an adhesive joint starts to develop. This ability can confer self-healing characteristics and high flexibility to reduce strain on adhesion joints and surrounding parts, such as in repaired fixtures or wounded tissue. At 50 s cure time, while BSA and unmodified $Mfp5^1$ had adhesion work values of less than 0.7 fJ µm$^{-1}$, $Mfp5^1_{DOPA}$ exhibited an adhesion work that was 3.3-fold higher than that of unmodified $Mfp5^1$ (FIG. 10B). Furthermore, $Mfp5^2_{DOPA}$ and $Mfp5^3_{DOPA}$ had adhesion energies that were 10.5- and 19.2-fold higher than that of $Mfp5^1_{DOPA}$, respectively, also exhibiting a chain-length-dependent increase.

Figure 12:
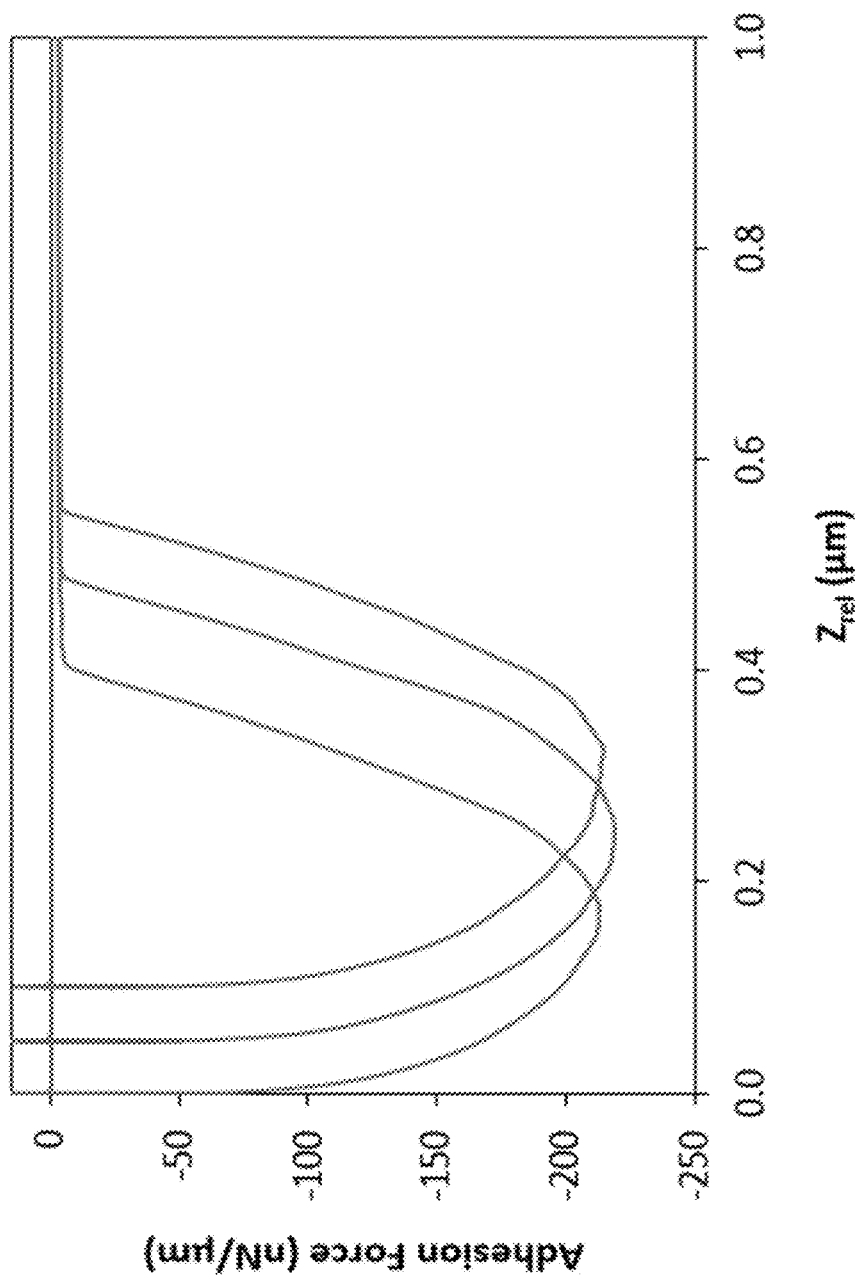
FIG. 12 is an exemplary embodiment of representative adhesion force curves for Mfp$5^3_{DOPA}$ in accordance with the present disclosure.
Figure 13A:
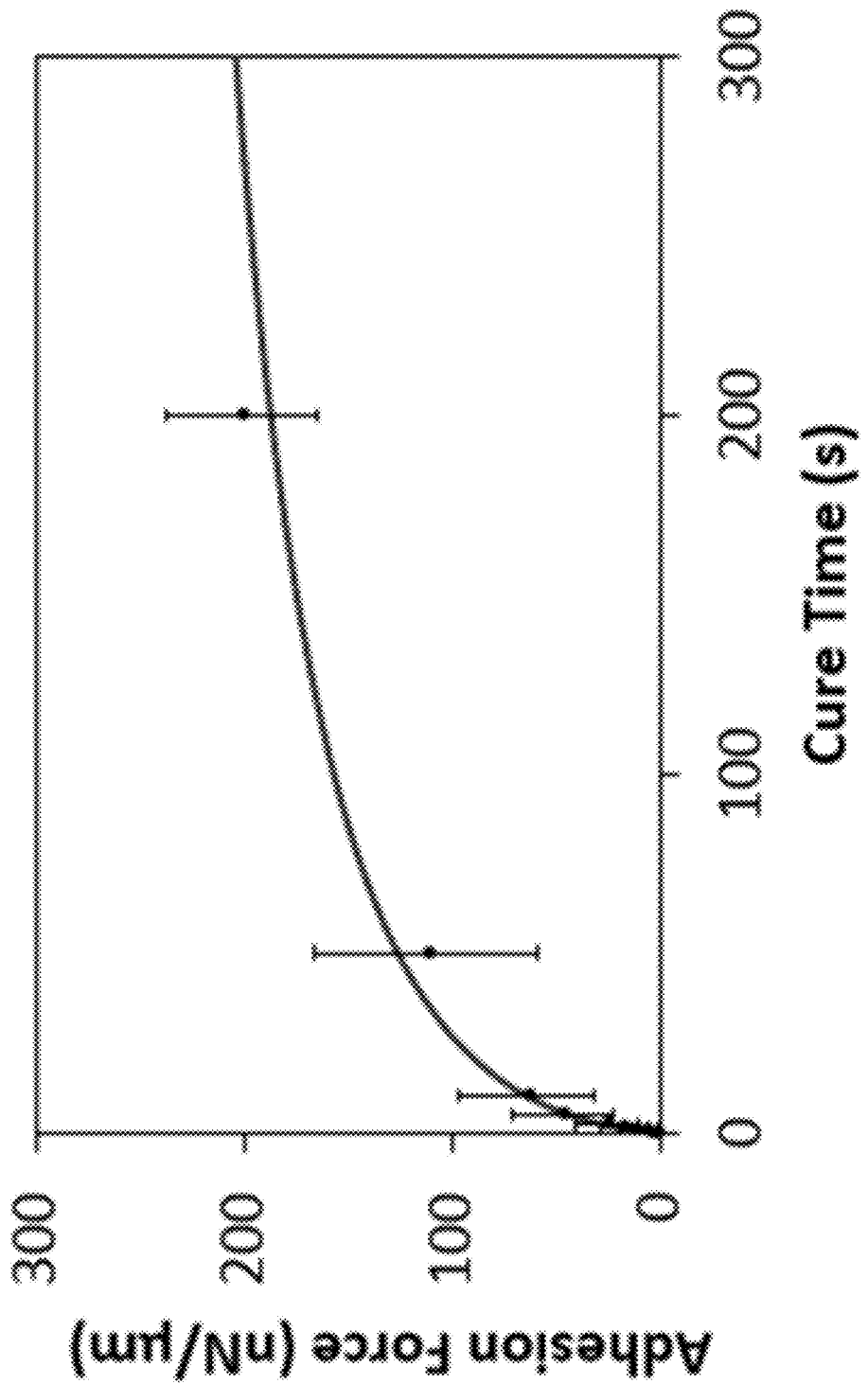
FIG. 13A is an exemplary embodiment of measured adhesion forces of Mfp$5^3_{DOPA}$ fitted to a logistic fit plotted on a linear scale in accordance with the present disclosure.
Figure 13B:
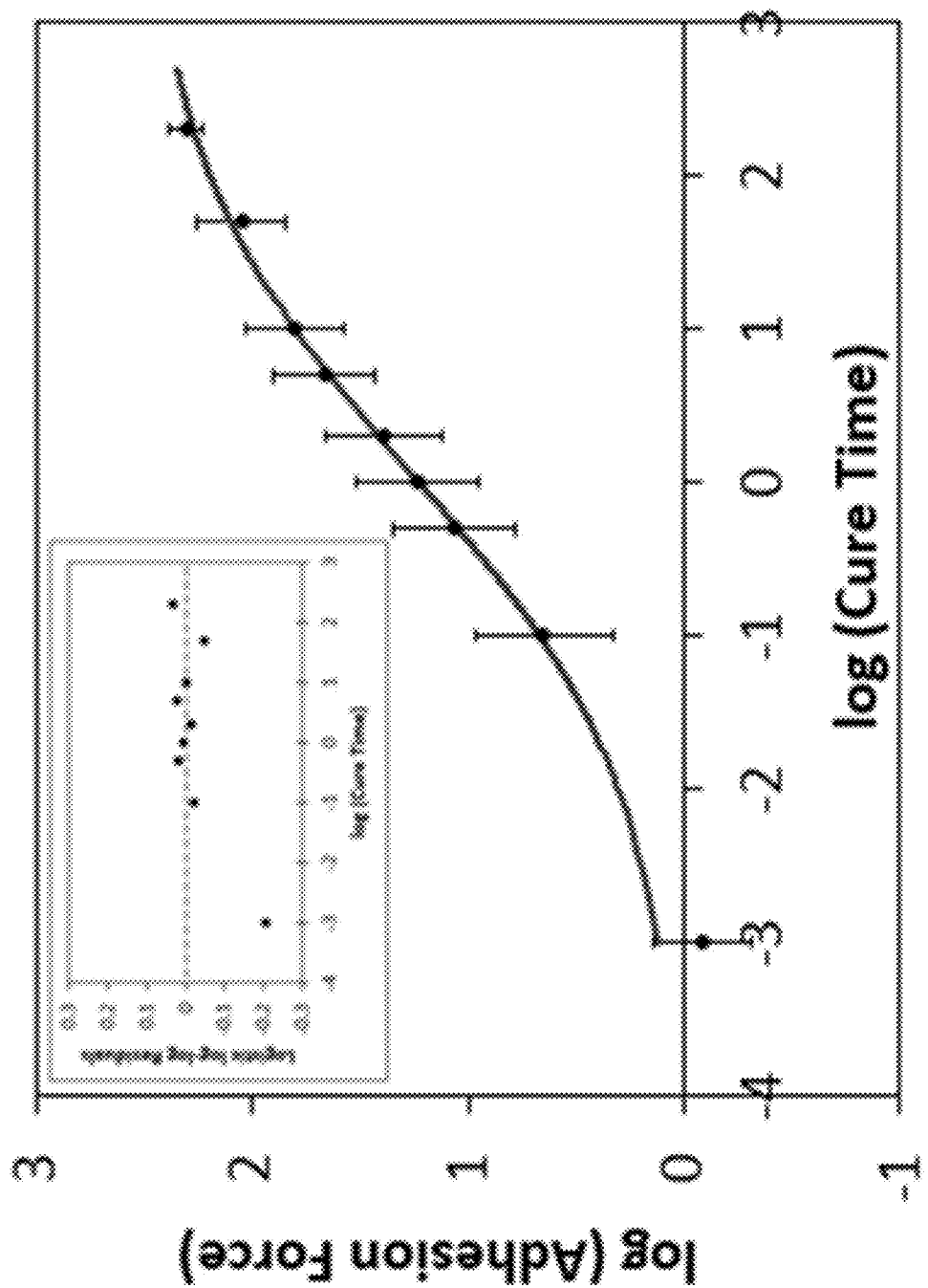
FIG. 13B is an exemplary embodiment of measured adhesion forces of Mfp$5^3_{DOPA}$ fitted to a logistic fit plotted on a log scale in accordance with the present disclosure.

The longest curing time that allowed a reliable approach-retract curve measurement for $Mfp5^3_{DOPA}$ was 200 s, because longer cure times produced adhesion strengths that were too high and prevented recovery of retract curves, even at the maximum AFM probe separation of our equipment (1 µm). At a cure time of 200 s, $Mfp5^3_{DOPA}$ exhibited an adhesion force of ~201 nN µm$^{-1}$ and an adhesion work of ~68 fJ µm$^{-1}$, values which are higher than previously reported for Mfp-mimetic adhesives (FIG. 12). FIG. 12 shows three representative adhesion force curves for $Mfp5^3_{DOPA}$ measured for longer cure times of 200 seconds. $Z_{rel}$ describes the separation distance between surfaces relative to the point of maximum contact. FIGS. 13A and 13B show the measured adhesion forces of $Mfp5^3_{DOPA}$ (black dots) at multiple cure times fitted to a logistic fit (red curves) and plotted on a linear (FIG. 13A) or log scale (FIG. 13B). Error bars represent standard deviations (n≥21). Inset in (b) shows non-patterned residuals to confirm the quality of the fit. Fitting the time course of adhesion force indicates that by 6 hours, $Mfp5^3_{DOPA}$ would achieve 75% of its theoretical maximum adhesion force of 343 nN µm$^{-1}$ (FIGS. 13A-B), far exceeding the adhesive capabilities of previously reported materials. Furthermore, at a cure time of 200 s, the separation distance at which maximal adhesion force was reached was 250±40 nm, which is 2.8-fold longer than the length of a fully extended $Mfp5^3_{DOPA}$ chain (90.3 nm), indicating that the adhesion force was contributed by cohesive protein-protein interaction.

Protein-protein interactions confer high cohesion, and thus overall adhesion between two surfaces. To analyze protein absorption to one surface, the Mfps disclosed herein were subjected to steady shear-flows in phosphate-buffered saline (PBS) buffer and quantified adsorbed protein amounts using a quartz crystal microbalance with dissipation monitoring (QCM-D). According to polymer physics, these conditions should lead to physical chain disentanglement, resulting in a thin and disperse protein layer from a soluble protein solution.

Figure 14A:
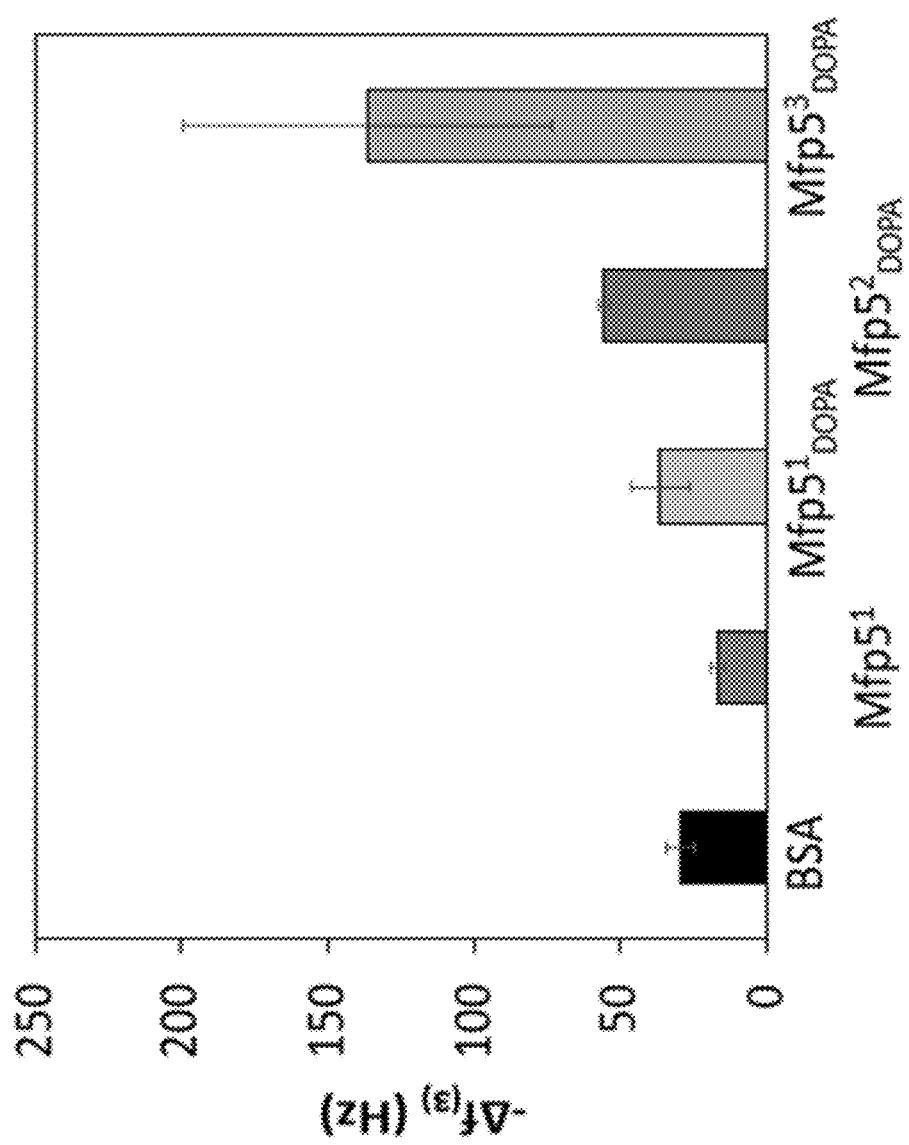
FIG. 14A is an exemplary embodiment of QCM analysis of protein adsorption with respect to the change in normalized third frequency ($-\Delta f_{(3)}$) in accordance with the present disclosure.
Figure 14B:
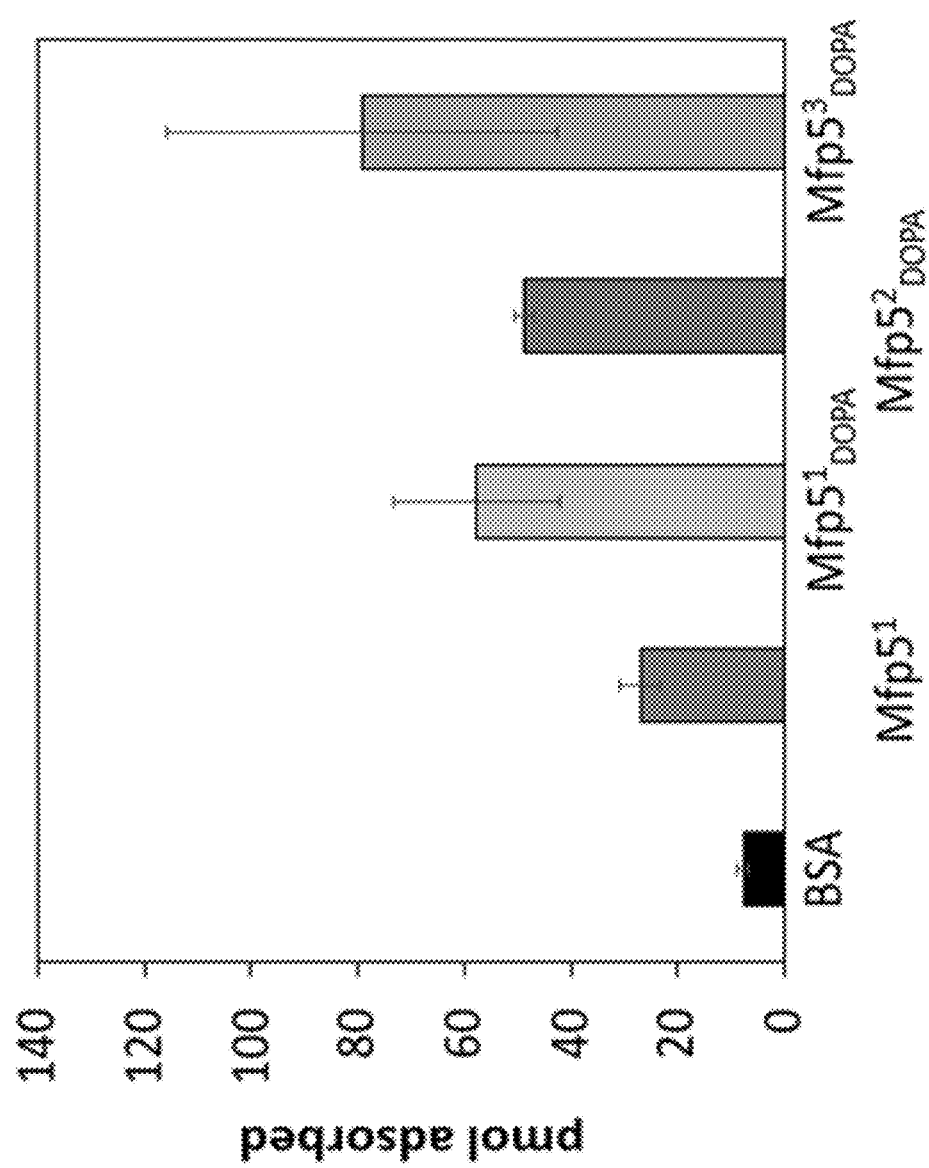
FIG. 14B is an exemplary embodiment of QCM analysis of protein adsorption with respect to number of moles of protein absorbed to the QCM sensor in accordance with the present disclosure.

FIG. 14A shows QCM analysis of protein adsorption the change in normalized third frequency ($-\Delta f_{(3)}$) after washing and re-establishment of a new steady state, are plotted for each protein sample. The values and error bars represent the means and standard deviations, respectively (n=3). Compared to the BSA and unmodified Mfp5$^1$ negative controls, all DOPA-modified Mfps exhibited significantly higher decreases in quartz crystal resonance frequency (FIG. 14A), indicating greater mass of protein adsorbed to the gold-coated quartz sensor surface. The frequency changes in Mfp5$^3_{DOPA}$ and Mfp5$^2_{DOPA}$ were 3.6- and 1.5-fold higher, respectively, than in Mfp5$^1_{DOPA}$. However, when normalized to the moles of protein molecules, all DOPA-modified proteins exhibited a higher shift of frequency than unmodified Mfp5 and BSA, but had similar surface densities for different molecular weights (FIG. 14B). FIG. 14B shows QCM analysis of protein adsorption with respect to the number of moles of protein absorbed to the QCM sensor. The values and error bars represent the means and standard deviations, respectively (n=3). If a single protein layer is formed and fully occupies the surface of the gold-coated quartz crystal surface, the moles of proteins adsorbed per area are expected to decrease as molecular weight increases. AFM results disclosed herein suggest that protein layers increased with Mfp molecular weight. These two opposing trends may cancel each other out leading to similar moles of protein absorbed per unit area.

In accordance with the present disclosure, *E. coli* was successfully engineered to produce Mfp5-based adhesive proteins with strong underwater adhesion capabilities. Under the experimental conditions, Mfp5$^3_{DOPA}$ displayed high adhesion forces and adhesion works that were comparable to or higher than previously reported Mfp-mimetic adhesives. With a longer curing time, the adhesion force of Mfp5$^3$ could be even higher than what was measured, but was beyond the detection limit of the method disclosed herein. Such adhesive proteins can potentially be used to replace natural Mfps in a variety of applications, with even better performance due to their stronger underwater adhesion. The results demonstrated that protein-protein cohesive interactions play an important role in determining both adhesion force and adhesion work. Positive correlations were observed between Mfp5's molecular weight and its measured adhesion force and adhesion work. These correlations indicate that producing high molecular weight proteins might be a natural strategy to obtain extensive cohesive interactions, as evidenced in Mfp2 and Mfp4, which have the highest molecular weights within the byssal plaque core (45 kDa and 90 kDa, respectively) among all Mfps and play cohesive roles in mussel plaques. The observed molecular weight dependent adhesion can be used in design rules to guide future engineering efforts, creating even stronger underwater adhesives.

In some embodiments, a Mfp is disclosed comprising a full length polypeptide sequence from a mussel species, a partial polypeptide sequence from a mussel species, or combinations thereof. In some embodiments, the Mfp is selected from the group consisting of Mfp1, Mfp2, Mfp3, Mfp4, and Mfp5.

In some embodiments, the Mfp is an oligomer protein comprising a plurality of repeats of the Mfp within one protein molecule. In some embodiments, the oligomer protein is synthesized from a mixture of a Mfp-Int$^N$ fusion protein and an Int$^C$-Mfp fusion protein. In some embodiments, the Mfp-Int$^N$ fusion protein is produced by fusing an N-terminal split intein (Int$^N$) to a first Mfp repeat, and the Int$^C$-Mfp fusion protein is produced by fusing a C-terminal split intein (Int$^C$) to a second Mfp repeat.

In some embodiments, the first Mfp repeat is Mfp5$^2$, and the second repeat is Mfp5$^1$. In some embodiments, the oligomer protein is Mfp5$^3$, the Mfp-Int$^N$ fusion protein is Mfp5$^2$-Int$^N$, and the Int$^C$-Mfp fusion protein is Int$^C$-Mfp5$^1$.

In some embodiments, the first Mfp repeat is Mfp5$^1$, and the second repeat is Mfp5$^2$. In some embodiments, the oligomer protein is Mfp5$^3$, the Mfp-Int$^N$ fusion protein is Mfp5$^1$-Int$^N$, and the Int$^C$-Mfp fusion protein is Int$^C$-Mfp5$^2$. In some embodiments, the Int$^N$ and Int$^C$ are from a Cfa split intein (SI). In some embodiments, the Mfp-Int$^N$ fusion protein and the Int$^C$-Mfp fusion protein are separately expressed from *E. coli*.

EXPERIMENTAL SECTION

Chemicals and Reagents. Unless otherwise noted, all chemicals and reagents were obtained from Millipore Sigma (Saint Louis, Mo., USA). Plasmid purification and gel extraction kits were purchased from iNtRON Biotechnology (Seoul, South Korea). FastDigest restriction enzymes and T4 DNA ligase were purchased from Thermo Fisher Scientific (Austin, Tex., USA) and were used according to the suggested protocols from the manufacturer.

Plasmid Construction. A BioBrick system was used to facilitate cloning of two-part split intein-fused material protein domains. This system takes the following conditions into account: (a) split intein genes, ribosome binding sites (RBS), 5'-untranslated regions (5'-UTR), antibiotic resistance markers, promoters, and origins of replication are flanked with appropriate restriction sites that allow them to be easily swapped with other corresponding genes of interest, (b) restriction sites that exist within open reading frames introduce amino acids that are small, flexible, and are not expected to change the protein behavior and dynamics, (c) restriction sites are all distinct with respect to one another to facilitate the assembly of complete plasmids in one pot and in one step. All restriction sites used are schematically mapped out in FIGS. 2A-C and 3A-D.

*E. coli* strain MDS42pdu was used as a host strain for cloning of all genes and plasmids in this study. The amino acid sequences of *Mytilus galloprovincialis* Mfp5$^1$, Mfp5$^2$, and Mfp5$^3$ were codon-optimized for *E. coli* expression using the Gene Designer 2.0 software package (DNA 2.0 Inc.). All designed DNA sequences were chemically synthesized by Integrated DNA Technologies Inc. (San Jose, Calif., USA) (Table 1). These synthetic genes were then amplified using polymerase chain reaction (PCR) with corresponding forward and reverse primers as listed in Table 2. All mfp5 genes were amplified with BglII and BamHI sites on the 5' and 3' ends, respectively, for insertion into the pE7a-AKTK-H6 backbone (AKTK is SEQ ID NO: 19) containing the same sites, which was previously PCR amplified from plasmid pE7a-GFP1, with the addition of short coding sequences, 5'-ATGGCTAAGACTAAACATCAT-CACCATCATCAC-3'(SEQ ID NO: 1), translating to N'-MAKTK-H6-C' (SEQ ID NO: 2) (FIGS. 7A-B). The AKTK (SEQ ID NO: 19) expression tag, immediately following the start codon has been shown to increase translation initiation rates and the N-terminal hexahistidine-tag (His6) was used for downstream protein purification. This backbone was named pE7a-AKTK-H6 (AKTK is SEQ ID NO: 19). The amplified gene and backbone were digested with BglII and BamHI. The backbone was further treated with alkaline phosphatase to minimize unwanted recircularization. The digested backbone and gene inserts were then ligated with T4 ligase. The proper orientation of each gene within the isolated plasmid was confirmed with restriction digestion using BglII and BamHI followed by Sanger sequencing (Eurofins Genomics, Louisville, Ky., USA).

To construct plasmids containing split intein-fused Mfp5 proteins, the amino acid sequences of Cfa N- and C-inteins ($Cfa^N$ and $Cfa^C$, respectively) were first codon-optimized and chemically synthesized using the same method as described above. The synthesized gene containing the $Cfa^N$ domain, which is flanked by NdeI and KpnI sites, and the $Cfa^C$ domain, which is flanked by Kpn2I and XhoI sites, were digested directly from the synthesized DNA. The mfp52 and mfp51 genes were amplified with corresponding primers (Table 2) containing KpnI and Kpn2I restriction sites. Amplified mfp52 and mfp51 fragments were digested (FIGS. 2A-C) and ligated with $Cfa^N$ and $Cfa^C$ into pE7a-N'-AKTK (AKTK is SEQ ID NO: 19) and pE7a-$H_{10}$-C' backbones, respectively. The corresponding backbones were both PCR amplified and contain distinct restriction sites for ligation of the appropriate genes in the correct locations (FIGS. 2A-C).

Expression of Recombinant Proteins. E. coli strain BL21 (DE3) (Thermo Fisher Scientific, Waltham, Mass.) was used as a host strain for expression of Mfps. E. coli strains containing the plasmids listed in Table 3 were cultured in shake flasks with Luria-Bertani (LB) broth containing 10 g/L tryptone, g/L sodium chloride, and 5 g/L yeast extract with the appropriate antibiotic (100 µg/mL ampicillin). Fresh transformants were cultivated overnight in 50 mL LB medium at 37° C. Overnight cultures were then used to inoculate 1 L fresh LB medium in Erlenmeyer flasks at an initial OD600=0.08. Cultures were grown at 37° C. with shaking to OD600=0.6, then induced by addition of 500 µM (for Mfp5¹ and $Cfa^C$-Mfp5¹) or 50 µM (Mfp5² and Mfp5²-$Cfa^N$) IPTG. The culture was further cultivated at 37° C. at 250 rpm for another 5-7 hours. Cells were harvested by centrifugation at 4,500×g for 20 min at 4° C. Centrifuged cell pellets were either directly extracted or stored at −80° C. until needed.

Protein Purification. For Mfp5¹ and Mfp5², cell pellets were resuspended in 10 mL of guanidine lysis buffer (6 M guanidine hydrochloride (BioBasic Inc., Amherst, N.Y., USA), 50 mM potassium phosphates, and 300 mM sodium chloride at pH 7.4) per gram of wet cells and lysed by agitation at 250 rpm. The lysates were centrifuged at 20,000×g for 20 min at 18° C. To reduce the viscosity, collected lysates were further sonicated on ice (to maintain a roughly ambient temperature) for 30 minutes with a QSonica probe sonicator using 5 seconds on/5 seconds off cycles. The lysates were filtered through 0.2 µm filter membranes. Both proteins were purified using an AktaPure Fast Protein Liquid Chromatograph (FPLC, GE Healthcare Inc., Chicago, Ill., USA) equipped with a 5 mL nickel affinity chromatography column (GE Healthcare). The column was pre-equilibrated with guanidine lysis buffer followed by sample loading. After washing with 5-10 column volumes (CVs) of guanidine wash buffer (6 M guanidine hydrochloride, 50 mM potassium phosphates, 300 mM sodium chloride, and 50 mM imidazole at pH 7.4), proteins were eluted and fractionated with 5-10 CVs of guanidine elution buffer (6 M guanidine hydrochloride, 50 mM potassium phosphates, 300 mM sodium chloride, and 250 mM imidazole at pH 7.4). Purified Mfp5¹ and Mfp5² proteins were examined by SDS-PAGE as shown in FIG. 4 and FIG. 5B.

Split-Intein Mediated Ligation and Purification of Mfp5³. Cell pellets containing $Cfa^C$-Mfp5¹ and Mfp5²-$Cfa^N$-His10 fusion proteins were separately resuspended in 10 mL of urea lysis buffer (8 M urea, 100 mM sodium phosphates, and 300 mM sodium chloride at pH 7.4) per gram of wet cells and lysed by agitation at 250 rpm overnight. The lysates were centrifuged at 20,000×g for 20 min at 18° C. Clear cell lysate was then mixed at a final reactant ratio of 4:1 ($Cfa^C$-Mfp5¹: Mfp5²-$Cfa^N$-His10) based on densitometric analysis of Coomassie Blue-stained SDS-PAGE gels. The excess $Int^C$-Mfp5¹ does not contain His-tag, thus can be easily separated from the ligated product. The lysate mixture was stirred at 30° C. for 8 hours. The mixed lysate was then filtered through a 0.2 µm filter membrane and purified by nickel affinity chromatography as described above.

Post-Translational Modification with Tyrosinase. Purified protein solutions were first dialyzed against 100 mM sodium acetates buffer at pH 5.5 using a 10 kDa molecular weight cut off (MWCO) dialysis membrane (Thermo Fisher Scientific). Dialyzed proteins were then diluted to a concentration of 4 mg/mL in 100 mM sodium acetates buffer at pH 5.5 with 100 mM ascorbic acid and filtered. Tyrosinase was added to a final concentration of 250 U $mL^{-1}$, and the mixture was incubated at 37° C. with agitation at 250 rpm for 30 minutes. After the reaction, the solution was filtered, and the enzyme activity in the flow-through was quenched by adding 0.2 mL of 6 N HCl per mL of reaction. The solution was filtered a final time and then was dialyzed extensively in 5% acetic acid at 4° C. and lyophilized.

Matrix-Assisted Laser Desorption/Ionization-Time of Flight (MALDI-TOF) Mass Spectrometry (MS) Analysis. Purified proteins at a final concentration of ~10 µM in 0.1 v/v %. trifluoroacetic acid (TFA) solution were mixed with dihydroxyacetophenone (DHAP) and spotted on a stainless steel MALDI target plate. Samples were analyzed using a Shimadzu AXIMA Resonance MALDI-TOF Mass Spectrometer (Shimadzu, Columbia, Md., USA) at the Saint Louis University Protein Core Facility. Positive-ion mass spectra analysis was conducted in standard linear mode with a laser power/acceleration voltage of 60-100 volts. The quadruple ion trap available for MS analysis was limited by a maximum m/z ratio of 15 kDa. For $Mfp5^1_{DOPA}$ with an expected molecular weight of 10978.02 Da, the single- and double-charged state peaks could be assigned at m/z values of 5489.01 and 3659.34, respectively (FIGS. 6A-B). For $Mfp5^2_{DOPA}$ with an expected molecular weight of 19793.86 Da, only the double-charged state peak could be assigned at an m/z value of 9896.93 (FIGS. 7A-B). For $Mfp5^3_{DOPA}$ with an expected molecular weight of 29849.88 Da, a triple-charged state was necessary to identify a signal within the measurable m/z range; however, this species was not clearly discernible from the noise and minor contaminants existing in this sample (data not shown).

Figure 15:
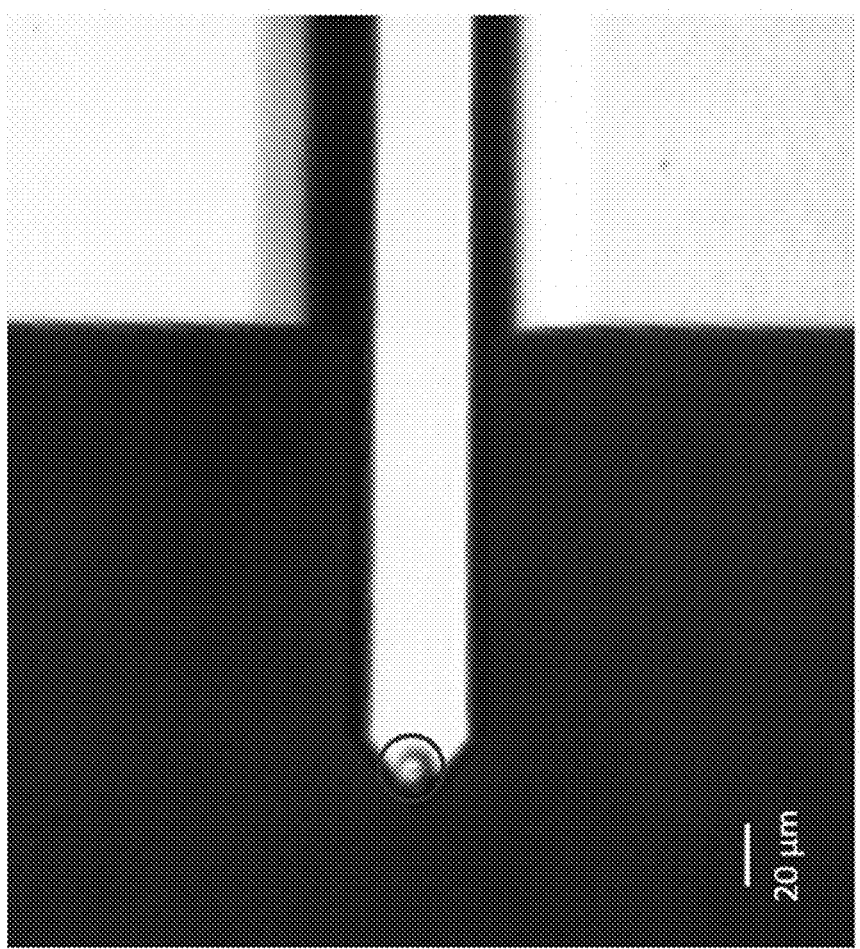
FIG. 15 is an exemplary embodiment of a light microscope image of a colloidal probe AFM cantilever used for adhesion measurements in accordance with the present disclosure.

AFM Colloidal Probe Analysis. Peak Force Tapping-Atomic Force Microscopy (PFT-AFM) was used to characterize the protein samples by measuring adhesion force and adhesion works using a colloidal probe AFM cantilever (FIG. 15). FIG. 15 shows a light microscope image of a colloidal probe AFM cantilever used for adhesion measurements. The colloidal probe used (circled in red) is a glass bead of radius 5 µm. This type of measurement is known as asymmetric adhesion where protein is bound firmly on the mica surface upon sample preparation and binds temporarily to the glass probe upon measurement, as outlined in previous studies. PFT mode was performed using a Bruker Multimode 8-High Resolution AFM (Bruker Inc., Billerica, Mass., USA) with calibrated glass colloidal probe cantilevers (radii of 5 μm and spring constants between 5.4 and 16 N m$^{-1}$, Novascan, Ames, Iowa, USA). Force curves were measured at a frequency of 1.0 Hz. Analysis of force curves was performed using the Nanoscope Analysis 1.8 software (Bruker Inc.). For each protein sample, force curves were collected in triplicate in at least 7 regions to comprehensively assess each sample.

For sample preparation, 10 μL of protein solution in PBS buffer was pipetted on a mica surface and set quiescently for 30 minutes. After extensive washing, the mica surface was mounted on the AFM stage and the adsorbed protein was probed under a buffered condition (100 mM sodium phosphates pH 7.4). Bovine serum albumin (BSA) and unmodified Mfp5$^1$ were used as controls and measured under the same condition.

Approach curves were fitted to the Alexander-de Gennes (AdG) model:

$$F(Z) = \frac{16\pi k_B T R L}{35 s^3}\left[7\left(\frac{2L}{Z+2h}\right)^{\frac{5}{4}} + 5\left(\frac{Z+2h}{2L}\right)^{\frac{7}{4}} - 12\right] \quad (1)$$

where F is the measured adhesion force, Z is the measured separation distance, $k_B$ is the Boltzmann constant, T is the absolute ambient temperature (~298 K), R is the contact probe radius (5 μm). L, h, and s are fitted parameters that represent equilibrium film thickness, the offset distance that considers material compressibility upon maximum probe contact, and the average distance between occupied sorption sites, respectively. This model has been used to describe the interaction of random-coil polymers and proteins on surfaces. The data was fit using MATLAB. Data far beyond the fitted equilibrium thicknesses were not included in order to prevent misfitting at larger separation distances. All fitted data had correlation coefficients ($r^2$) of at least 99%.

The fitted equilibrium thickness (L) parameters were further compared with both the radii of gyration assuming random-coil configurations, $<R>$, and the end-to-end distances when the proteins are fully stretched out as rigid rods, $L_r$. These distances were calculated using the formulas:

$$<R> = \sqrt{N<l>^2} \quad (2)$$

and $$L_r = Nl \quad (3)$$

where N is the number of amino acids in the protein and l is the length of one amino acid (3.5 angstroms).

Figure 16:
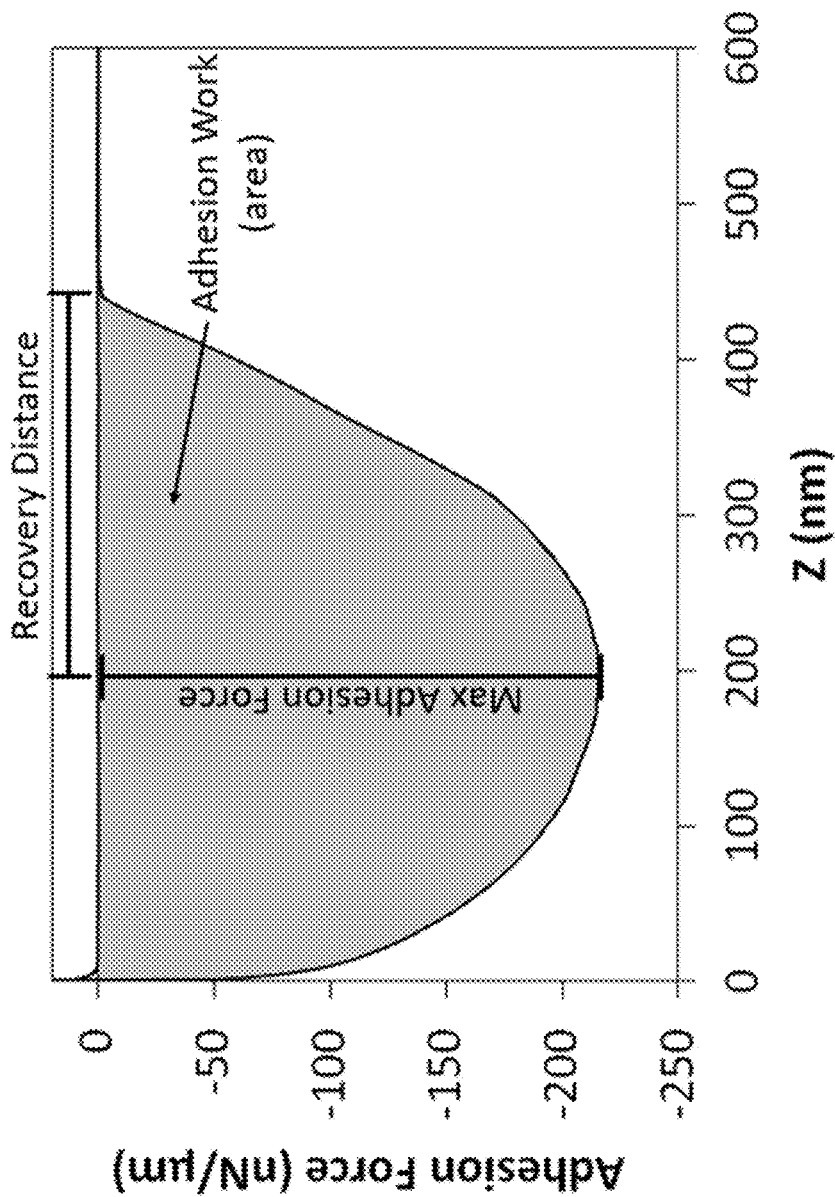
FIG. 16 is an exemplary embodiment of a schematic representation of maximum adhesion force, adhesion work, and recovery distance in accordance with the present disclosure.
Figure 17A:
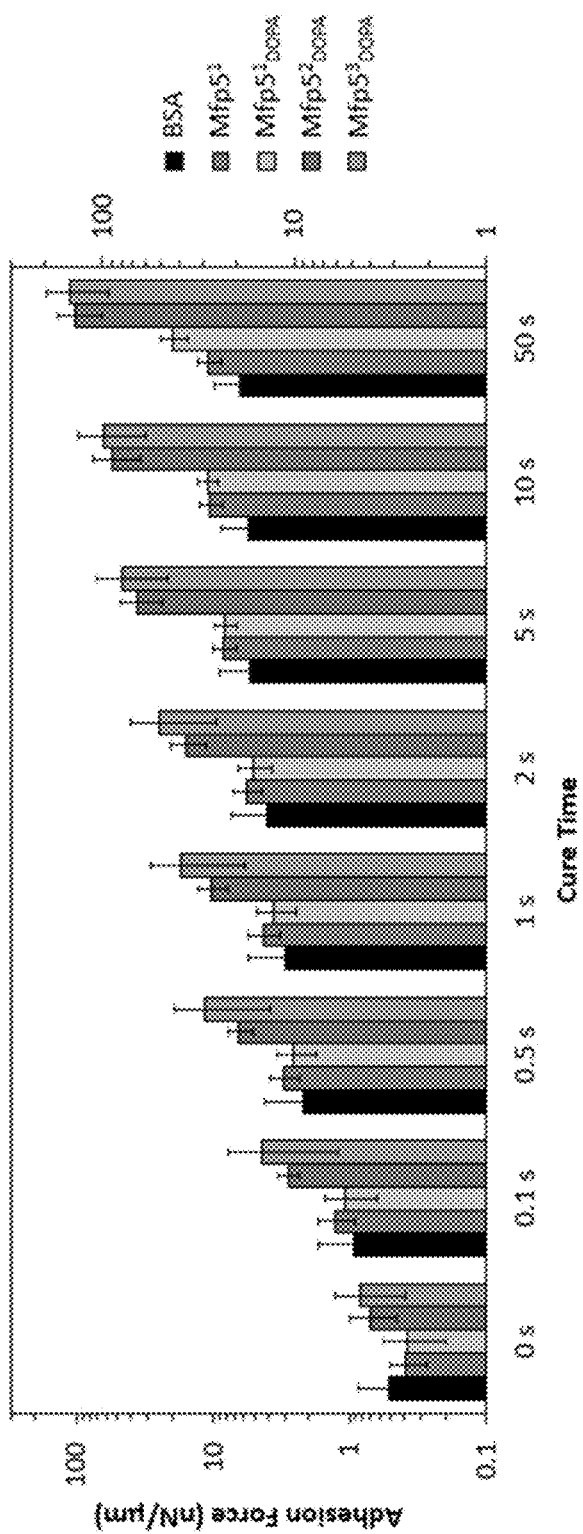
FIG. 17A is an exemplary embodiment of normalized adhesion force in accordance with the present disclosure.
Figure 17B:
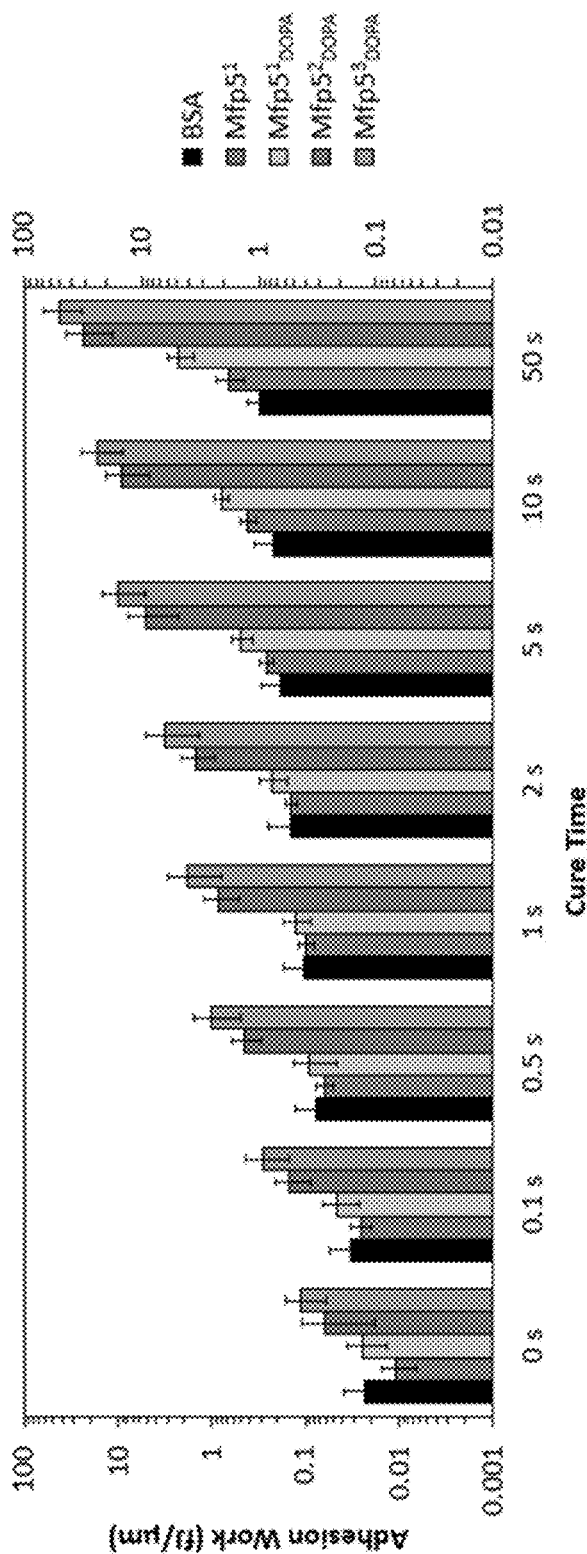
FIG. 17B is an exemplary embodiment of normalized adhesion work in accordance with the present disclosure.

Following probe approaching, the probe was cured on the protein sample for a delay time varying from 0 to 50 seconds for most measurements. The adhesion force was taken at the point of maximum force (most negative force). The adhesion work was calculated as the area "under" the retraction curve, relative to the zero nN baseline (FIGS. 8A-D, 10A-B, 16, and 17A-B). FIG. 16 shows a schematic representation of maximum adhesion force, adhesion work, and recovery distance. Normalized adhesion force (FIG. 17A) and adhesion work (FIG. 17B) is shown for all cure times ranging from 0 s to 50 s for all proteins tested. Error bars represent standard deviations (n≥21).

For the strongest oligomer tested, Mfp5$^3$$_{DOPA}$, adhesion forces with each respective cure time tested were averaged and fit to a logistic model of the form:

$$\log F = \frac{A}{1 + BQ^{\log t}} \quad (4)$$

where F is the measured adhesion force, t is the cure time, and A, B, and Q are fitted constants. This model was appropriate given the assumption that an infinitesimally small cure time would result in zero adhesion force, while an infinite cure time would result in a theoretical maximum adhesion force (represented by the fit constant 'A') upon complete underwater curing of the material. The log-log scaling of the adhesion force and cure time axes allowed for the fitted model to give rise to an unpatterned residual, which indicates a high quality of fitting (FIG. 13B).

Figure 18A:
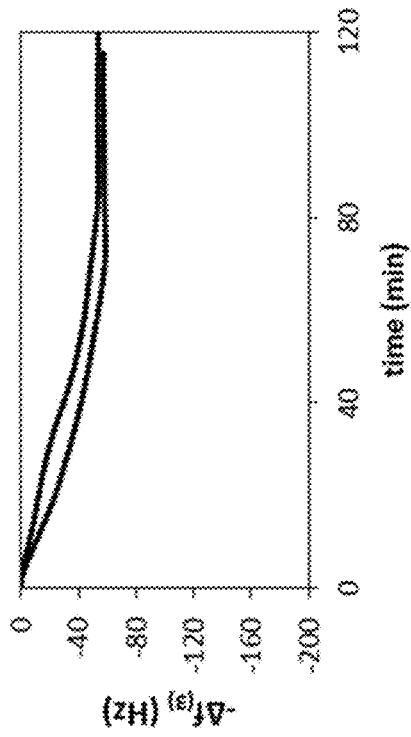
FIG. 18A is an exemplary embodiment of QCM curves for a BSA control in accordance with the present disclosure.
Figure 18B:
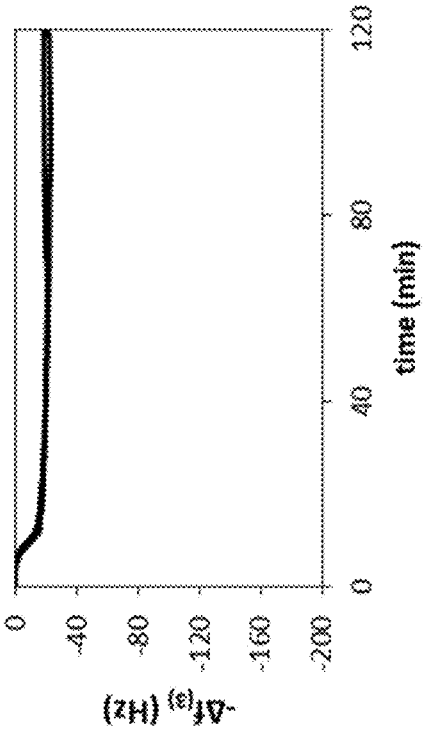
FIG. 18B is an exemplary embodiment of QCM curves for an unmodified Mfp$5^1$ control in accordance with the present disclosure.
Figure 18C:
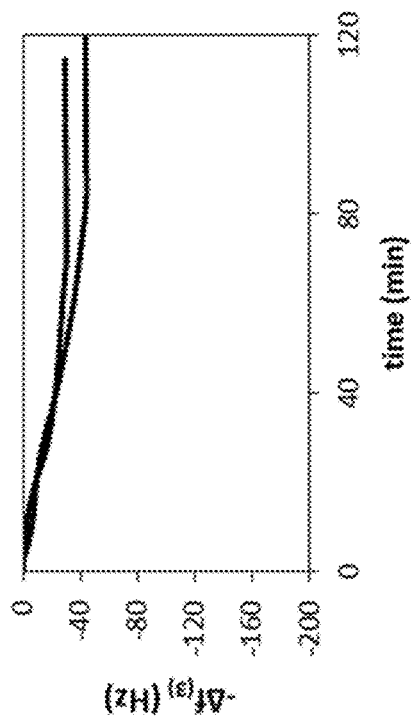
FIG. 18C is an exemplary embodiment of QCM curves for Mfp$5^1_{DOPA}$ in accordance with the present disclosure.
Figure 18D:
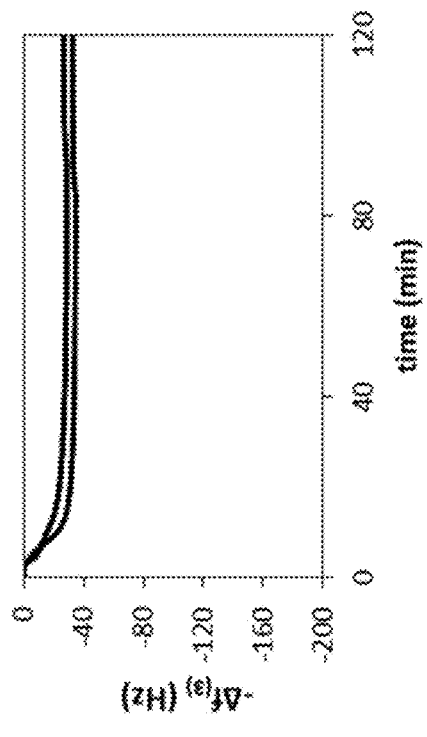
FIG. 18D is an exemplary embodiment of QCM curves for Mfp$5^2_{DOPA}$ in accordance with the present disclosure.
Figure 18E:
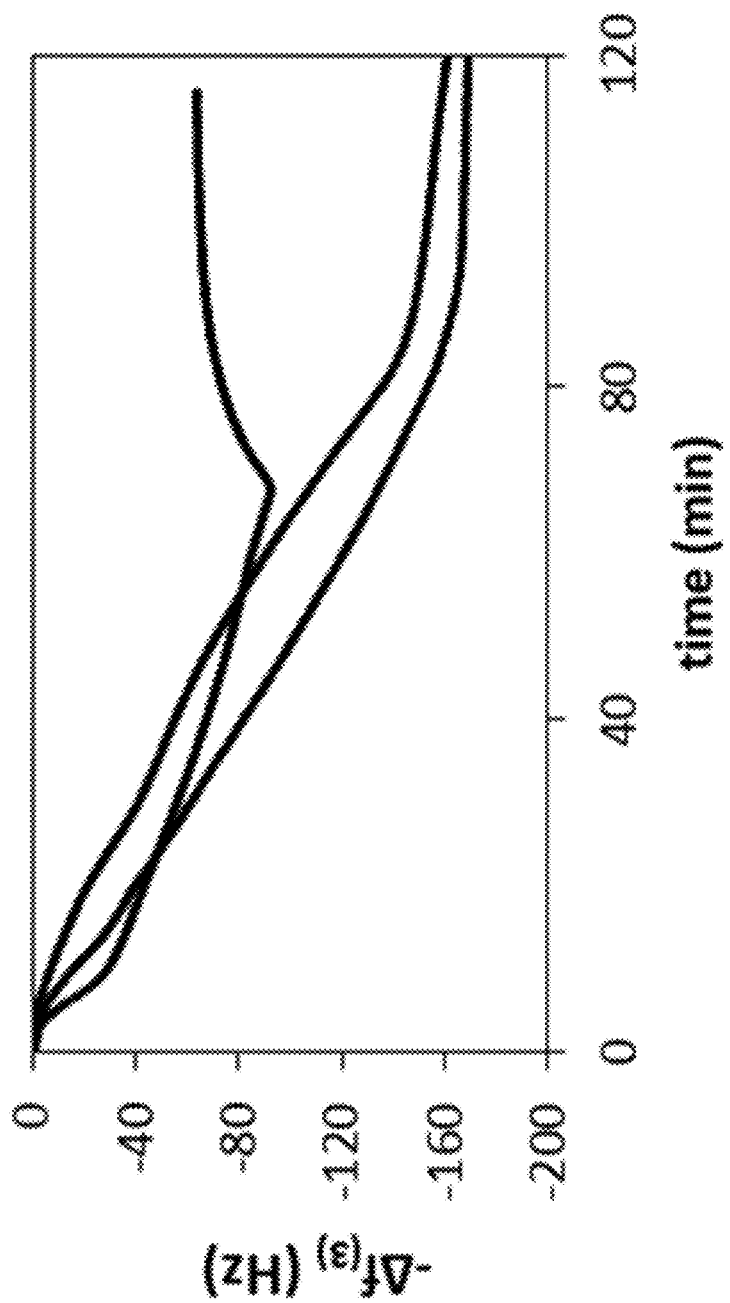
FIG. 18E is an exemplary embodiment of QCM curves for Mfp$5^3_{DOPA}$ in accordance with the present disclosure.

Quartz Crystal Microbalance with Dissipation Monitoring (QCM-D) Analysis. Gold-coated quartz crystal sensors (QSX 301, Biolin Scientific, Gothenburg, Sweden) were used for QCM analysis. The sensors were cleaned by UV irradiation for 15 minutes, heated in a mixture of ammonia (25%) and hydrogen peroxide (30%) at 75° C. for 5 minutes, then thoroughly rinsed with distilled water, dried with N2, and subjected to 10 minutes of UV irradiation before being mounted in the QCM flow modules (Biolin Scientific). PBS buffer carrier solution was flowed through an injector valve into the flow cell modules containing the quartz sensors at a flow rate of 0.1 mL min$^{-1}$ until stable baselines were achieved. Protein solutions were prepared to final concentrations of 10 μM (or 2 mg mL$^{-1}$ in the case of BSA) in PBS buffer (100 mM sodium phosphates pH 7.4) and flowed through the flow cell at a flow rate of 10 μL min$^{-1}$ for 60 minutes. PBS buffer carrier solution was flowed through to wash unbound protein off the quartz sensors until the frequency shift was stable (FIGS. 18A-E). FIGS. 18A-E depict QCM curves for all samples. Collected data from QCM, measuring changes in crystal resonance frequencies as a function of time elapsed while flowing solutions of a BSA control (FIG. 18A), an unmodified Mfp5$^1$ control (FIG. 18B), Mfp5$^1$$_{DOPA}$ (FIG. 18C), Mfp5$^2$$_{DOPA}$ (FIG. 18D), and Mfp5$^3$$_{DOPA}$ (FIG. 18E). At least 2 replicates were measured for each protein. Mfp5$^3$$_{DOPA}$ was measured in triplicate. The adsorbed mass was calculated using the Sauerbrey equation.

$$\Delta m = \frac{-\Delta f \cdot A \cdot \sqrt{\mu_{quartz}\rho_{quartz}}}{2 F_{quartz}^2} \quad (5)$$

where $\Delta m$ is change in mass, $\Delta f$ is change in crystal resonance frequency, A is the active area of the crystal between electrodes, $\mu_{quartz}$ is the shear modulus of the quartz crystal, $\rho_{quartz}$ is the density of the quartz crystal, and $F_{quartz}$ is the reference frequency. This equation can be simplified to:

$$\Delta m = -C \cdot \Delta f \quad (6)$$

where C (=17.7 ng cm$^2$ Hz$^{-1}$) is a constant that combines all constants relating to using gold-coated quartz sensors for deposition with the QCM instrument utilized herein.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

TABLE 1

Coding sequences

| Name | Sequence | Description |
|---|---|---|
| mfp5[1] (SEQ ID NO: 3) | GCTAAGACTAAACATCATCACCATCACCACGGT *GGCGGTGGCAGCAGATCTGGATCT*AGCAGCGAAG AGTATAAAGGTGGTTACTACCCGGGCAACACTTA CCACTACCATAGCGGCGGCTCCTACCACGGTTCC GGCTATCACGGTGGCTACAAAGGTAAATACTACG GCAAAGCGAAAAAGTACTACTACAAATATAAAA ACTCCGGCAAATACAAGTATCTGAAGAAGGCTC GTAAATATCACCGTAAAGGTTACAAAAAGTATTA CGGCGGTGGTTCTTCT*GGATCC* | Coding sequence encoding Mfp5[1] protein, which includes coding sequences for the AKTK (SEQ ID NO: 19) expression tag, His$_6$ affinity tag, and *linker & BioBrick cut sites* |
| mfp5[2] (SEQ ID NO: 4) | GCTAAGACTAAACATCATCACCATCACCACGGT *GGCGGTGGCAGCAGATCT*TCAAGTGAAGAATATA AGGGCGGCTATTACCCTGGGAACACCTACCATTA CCACTCGGGTGGTTCGTATCATGGTTCCGGCTAC CATGGTGGTTACAAGGGGAAGTATTATGGTAAA GCGAAGAAATACTATTACAAATACAAGAATTCTG GAAAGTATAAATATCTGAAAAAAGCTCGCAAAT ATCATCGTAAAGGATATAAAAAATACTATGGAG GTGGCAGTAGCAGTTCCGAAGAATATAAAGGGG GTTACTACCCTGGAAACACTTATCATTATCATAG TGGAGGTTCTTACCATGGCAGTGGATATCACGGC GGTTATAAGGGTAAGTATTATGGGAAAGCCAAA AAGTATTACTATAAGTACAAGAATTCTGGCAAAT ACAAGTACTTGAAGAAGGCTCGTAAGTACCACC GCAAAGGTTACAAGAAATACTATGGAGGCGGTT CAAGT*CTCGAG* | Coding sequence encoding Mfp5[2] protein, which includes coding sequences for the AKTK (SEQ ID NO: 19) expression tag, His$_6$ affinity tag, and *linker & BioBrick cut sites* |
| Cfa[N] (SEQ ID NO: 5) | AAAAAA*CATATG*GTCAAGATCATTAGTCGTAAGA GTCTGGGCACTCAAAACGTCTACGATATTGGAGT AGAAAAAGATCATAATTTTTTGCTGAAGAATGGG CTGGTGGCCTCTAACTGCTTCAACGGTACC | Codon optimized N-terminal SI$^C$ coding sequence for mfp5[3] assembly with mfp5 sequence, which includes the coding sequence for SI$^N$ native extein amino acids & KpnI restriction site |
| Cfa[C] (SEQ ID NO: 6) | TCCGGAGCAGAATATTGCCTGTCTTACGACACA GAGATTCTGACCGTTGAATATGGATTCCTTCCTA TCGGTAAGATCGTGGAGGAACGGATTGAATGCA CAGTCTATACGGTAGATAAAAATGGCTTTGTGTA TACACAACCTATTGCTCAGTGGCATAACCGGGGA GAACAGGAAGTTTTCGAATACTGCTTAGAAGACG GTTCGATTATCCGTGCAACGAAAGATCACAAATT TATGACGACCGACGGTCAGATGTTACCGATTGAT GAGATTTTCGAACGGGGGTTAGACCTGAAACAA GTTGATGGTTTGCCGTAA*GGATCC*AAAAAA | Codon optimized C-terminal SI$^N$ coding sequence for mfp5[3] assembly with mfp5[2] sequence, which includes the coding sequence for SI$^C$ native extein amino acids & Kpn2I restriction site |

TABLE 2

Primers

| Name | Sequence | Description |
|---|---|---|
| BglII-Mfp5[1]-F (SEQ ID NO: 7) | AAAAAAAGATCTAGCAGCGAAGAGTAT AAAGGTG | Forward primer for amplification of mfp5[1] with BglII overhang for insertion into pE7a-AKTK-H6 backbone (AKTK is SEQ ID NO: 19) |
| BamHI-Mfp5[1]-R (SEQ ID NO: 8) | AAAAAAGGATCCAGAAGAACCACCGCC G | Reverse primer for amplification of mfp5[1] with BamHI overhang for insertion into pE7a-AKTK-H6 backbone (AKTK is SEQ ID NO: 19) |
| BglII-Mfp5[2]-F (SEQ ID NO: 9) | AAAAAAAGATCTTCAAGTGAAGAATAT AAGGGCGGCTAT | Forward primer for amplification of mfp5[2] with BglII overhang for insertion into pE7a-AKTK-H6 backbone (AKTK is SEQ ID NO: 19) |
| XhoI-Mfp5[2]-R (SEQ ID NO: 10) | AAAAAACTCGAGACTTGAACCGCCTCC ATAGTATTTCTTG | Reverse primer for amplification of mfp5[2] with XhoI overhang for insertion into pE7a-AKTK-H6 backbone (AKTK is SEQ ID NO: 19) |

TABLE 2-continued

Primers

| Name | Sequence | Description |
|---|---|---|
| KpnI-Mfp5¹-F (SEQ ID NO: 11) | AAAAAAGGTACCAGCAGCGAAGAGTATAAAGGTGGTTACTACC | Forward primer for amplification of mfp5¹ with KpnI overhang for insertion into pE7a-SI backbone |
| Kpn2I-Mfp5¹-R (SEQ ID NO: 12) | AAAAAATCCGGAAGAAGAACCACCGCCGTAATAC | Reverse primer for amplification of mfp5¹ with Kpn2I overhang for insertion into pE7a-SI backbone |
| KpnI-Mfp5²-F (SEQ ID NO: 13) | AAAAAAGGTACCTCAAGTGAAGAATATAAGGGCGGCTATTACCC | Forward primer for amplification of mfp5² with KpnI overhang for insertion into pE7a-SI backbone |
| Kpn2I-Mfp5²-R (SEQ ID NO: 14) | AAAAAATCCGGAACTTGAACCGCCTCCATAGTATTTCTTGTAAC | Reverse primer for amplification of mfp5² with Kpn2I overhang for insertion into pE7a-SI backbone |

TABLE 3

Plasmids

| Name | ORI | Promoter | Resistance | Gene |
|---|---|---|---|---|
| pE7a | ColE1 | $P_{T7}$ | $Amp^R$ | N/A |
| pE7a-mfp5¹ | ColE1 | $P_{T7}$ | $Amp^R$ | $mfp5^1$ |
| pE7a-mfp5² | ColE1 | $P_{T7}$ | $Amp^R$ | $mfp5^2$ |
| pE7a-mfp5²-Cfa$^C$ | ColE1 | $P_{T7}$ | $Amp^R$ | $mfp5^2$ + Cfa$^C$ |
| pE7a-Cfa$^C$-mfp5¹ | ColE1 | $P_{T7}$ | $Amp^R$ | Cfa$^N$ + $mfp5^1$ |

TABLE 4

Strains

| Name | Genotype |
|---|---|
| MDS42pdu | MDS42 polB dinB umuDC |
| BL21(DE3) | F⁻ ompT gal dcm lon hsdS$_B$(r$_B^-$m$_B^-$) λ(DE3 [lacI lacUV5-T7p07 ind1 sam7 nin5]) [malB⁺]$_{K-12}$(λ$^S$) |
| sM-Mfp5 | MDS42pdu containing pE7a-mfp-5 |
| sM-Mfp5² | MDS42pdu containing pE7a-mfp-5² |
| sM-Mfp-5²-Cfa$^N$ | MDS42pdu containing pE7a-mfp-5²-Cfa$^N$ |
| sM-Cfa$^C$-mfp-5 | MDS42pdu containing pE7a-Cfa$^C$-mfp-5 |
| sB-Mfp5 | BL21(DE3) containing pE7a-mfp-5 |
| sB-Mfp5² | BL21(DE3) containing pE7a-mfp-5² |
| sB-Mfp-5²-Cfa$^N$ | BL21(DE3) containing pE7a-mfp-5²-Cfa$^N$ |
| sB-Cfa$^C$-Mfp-5 | BL21(DE3) containing pE7a-Cfa$^C$-mfp-5 |

TABLE 5

Protein sequences

| Name | Sequence | Description |
|---|---|---|
| Mfp5¹ (SEQ ID NO: 15) | AKTKHHHHHHGGGGSRSGSSSEEYKGGYYPGNTYHYHSGGSYHGSGYHGGYKGKYYGKAKKYYYKYKNSGKYKYLKKARKYHRKGYKKYYGGGSSGS | Mfp5 protein, which includes the AKTK (SEQ ID NO: 19) expression tag, His₆ affinity tag, and linker & BioBrick cut sites |
| Mfp5² (SEQ ID NO: 16) | AKTKHHHHHHGGGGSRSSSEEYKGGYYPGNTYHYHSGGSYHGSGYHGGYKGKYYGKAKKYYYKYKNSGKYKYLKKARKYHRKGYKKYYGGGSSSEEYKGGYYPGNTYHYHSGGSYHGSGYHGGYKGKYYGKAKKYYYKYKNSGKYKYLKKARKYHRKGYKKYYGGGSSLE | Mfp5² protein, which includes the AKTK (SEQ ID NO: 19) expression tag, His₆ affinity tag, and linker & BioBrick cut sites |
| Cfa$^N$ (SEQ ID NO: 17) | AEYCLSYDTEILTVEYGFLPIGKIVEERIECTVYTVDKNGFVYTQPIAQWHNRGEQEVFEYCLEDGSIIRATKDHKFMTTDGQMLPIDEIFERGLDLKQVDGLP | C-terminal SI$^N$ sequence for mfp5³ assembly with mfp5², which includes the SI$^N$ native extein amino acids |

TABLE 5-continued

| Protein sequences | | |
|---|---|---|
| Name | Sequence | Description |
| Cfa$^C$ (SEQ ID NO: 18) | VKIISRKSLGTQNVYDIGVEKDHNFLLK NGLVASNCFN | N-terminal SI$^C$ sequence for mfp5$^3$ assembly with mfp5, which includes the SI$^C$ native extein amino acids |

What is claimed is:

1. A synthetic Mfp5 mussel foot protein, wherein the synthetic Mfp5 mussel foot protein is an oligomer protein comprising a plurality of Mfp5 repeats that are covalently linked;
   wherein the oligomer protein is synthesized from a mixture comprising:
      a Mfp5-$Int^N$ fusion protein, formed from an N-terminal split intein-fused Mfp5 repeat; and
      an $Int^C$-Mfp5 fusion protein, formed from a C-terminal split intein-fused Mfp5 repeat;
   wherein the Mfp5-$Int^N$ fusion protein is produced by fusing an N-terminal split intein ($Int^N$) to a first Mfp5 repeat, and wherein the $Int^C$-Mfp5 fusion protein is produced by fusing a C-terminal split intein ($Int^C$) to a second Mfp5 repeat;
   wherein the first Mfp5 repeat is selected from the group consisting of SEQ ID NO: 15 and SEQ ID NO: 16; and
   wherein the second Mfp5 repeat is selected from the group consisting of SEQ ID NO: 15 and SEQ ID NO: 16.

2. The synthetic Mfp5 mussel foot protein of claim 1, wherein the $Int^N$ is a $Cfa^N$ protein consisting of SEQ ID NO: 17 and $Int^C$ is a $Cfa^C$ protein consisting of SEQ ID NO: 18.

3. The synthetic Mfp5 mussel foot protein of claim 1, wherein the Mfp5-$Int^N$ fusion proteins and the $Int^C$-Mfp5 fusion proteins are separately expressed from E. coli.

4. A method for producing a synthetic Mfp5 mussel foot protein oligomer, the method comprising:
   fusing an N-terminal split intein ($Int^N$) to a first Mfp5 repeat to produce a Mfp5-$Int^N$ fusion protein, wherein the first Mfp5 repeat is selected from the group consisting of SEQ ID NO: 15 and SEQ ID NO: 16, and wherein the $Int^N$ is an N-terminal Cfa split intein;
   fusing a C-terminal split intein ($Int^C$) to a second Mfp5 repeat to produce an $Int^C$-Mfp5 fusion protein, wherein the second Mfp5 repeat is selected from the group consisting of SEQ ID NO: 15 and SEQ ID NO: 16, and wherein the $Int^C$ is a C-terminal Cfa split intein; and
   mixing the Mfp5-$Int^N$ fusion protein and the $Int^C$-Mfp5 fusion protein to produce the synthetic Mfp5 mussel foot protein oligomer.

5. The method of claim 4, wherein the Mfp5-$Int^N$ fusion protein and the $Int^C$-Mfp5 fusion protein are separately expressed from E. coli.

6. The method of claim 4, wherein the $Int^N$ is a $Cfa^N$ protein consisting of SEQ ID NO: 17 and $Int^C$ is a $Cfa^C$ protein consisting of SEQ ID NO: 18.

7. The method of claim 4, further comprising reacting the synthetic Mfp5 mussel foot protein oligomer with tyrosinase.

8. A system for producing a synthetic Mfp5 mussel foot protein adhesive, the system comprising:
   a Mfp5-$Int^N$ fusion protein, formed from an N-terminal split intein-fused Mfp5 repeat; and
   an $Int^C$-Mfp5 fusion protein, formed from a C-terminal split intein-fused Mfp5 repeat;
   wherein the Mfp5-$Int^N$ fusion protein is produced by fusing an N-terminal split intein ($Int^N$) to a first Mfp5 repeat, and wherein the $Int^C$-Mfp5 fusion protein is produced by fusing a C-terminal split intein ($Int^C$) to a second Mfp5 repeat;
   wherein the first Mfp5 repeat is selected from the group consisting of SEQ ID NO: 15 and SEQ ID NO: 16; and
   wherein the second Mfp5 repeat is selected from the group consisting of SEQ ID NO: 15 and SEQ ID NO: 16.

9. The system of claim 8, wherein the $Int^N$ is a $Cfa^N$ protein consisting of SEQ ID NO: 17 and $Int^C$ is a $Cfa^C$ protein consisting of SEQ ID NO: 18.

10. The system of claim 8, wherein the $Int^N$ is a $Cfa^N$ protein consisting of SEQ ID NO: 17 and $Int^C$ is a $Cfa^C$ protein consisting of SEQ ID NO: 18.

11. The system of claim 8, wherein the Mfp5-$Int^N$ fusion protein and the $Int^C$-Mfp5 fusion protein are separately expressed from *E. coli*.

* * * * *

UNITED STATES PATENT AND TRADEMARK OFFICE
CERTIFICATE OF CORRECTION

| | | |
|---|---|---|
| PATENT NO. | : 11,530,245 B2 | Page 1 of 1 |
| APPLICATION NO. | : 16/554171 | |
| DATED | : December 20, 2022 | |
| INVENTOR(S) | : Zhang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 219 days.

Signed and Sealed this
Fourteenth Day of January, 2025

Derrick Brent
*Acting Director of the United States Patent and Trademark Office*